US009896718B2

(12) United States Patent
Cui et al.

(10) Patent No.: US 9,896,718 B2
(45) Date of Patent: Feb. 20, 2018

(54) HERBICIDE TOLERANT COTTON EVENT PDAB4468.18.07.1

(71) Applicant: Dow AgroSciences LLC, Indianapolis, IN (US)

(72) Inventors: Yunxing C. Cui, Carmel, IN (US); Raina King, Indianapolis, IN (US); Tina M. Kaiser, Carmel, IN (US); Andrew E. Robinson, Brownsburg, IN (US); Dayakar Pareddy, Carmel, IN (US); Sandra G. Toledo, West Lafayette, IN (US); Leon B. Braxton, Travlers Rest, SC (US); David M. Anderson, Visalia, CA (US); Terry R. Wright, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 1017 days.

(21) Appl. No.: 13/748,402

(22) Filed: Jan. 23, 2013

(65) Prior Publication Data

US 2013/0191938 A1 Jul. 25, 2013

Related U.S. Application Data

(60) Provisional application No. 61/589,602, filed on Jan. 23, 2012.

(51) Int. Cl.

| | |
|---|---|
| ***C12N 15/82*** | (2006.01) |
| ***C12N 5/04*** | (2006.01) |
| ***C12N 15/11*** | (2006.01) |
| ***C12N 15/31*** | (2006.01) |
| ***A01H 5/10*** | (2006.01) |
| ***C12Q 1/68*** | (2018.01) |
| ***A01H 1/04*** | (2006.01) |

(52) U.S. Cl.

CPC ............ *C12Q 1/6813* (2013.01); *A01H 1/04* (2013.01); *C12N 15/8274* (2013.01); *C12N 15/8277* (2013.01); *C12Q 1/6895* (2013.01); *C12Q 2600/16* (2013.01)

(58) Field of Classification Search

None

See application file for complete search history.

(56) References Cited

U.S. PATENT DOCUMENTS

| | | | | |
|---|---|---|---|---|
| 7,557,201 B2 * | 7/2009 | Fincher | C12N 15/8261 536/23.6 |
| 2004/0117878 A1 * | 6/2004 | Bridge | A01H 5/10 800/314 |
| 2010/0251432 A1 | 9/2010 | Lira et al. | |
| 2011/0195845 A1 | 8/2011 | Lira et al. | |
| 2011/0203017 A1 | 8/2011 | Wright et al. | |

FOREIGN PATENT DOCUMENTS

| | | | |
|---|---|---|---|
| CN | 101027396 | 8/2007 | |
| CN | 101553111 | 10/2009 | |
| CN | 101680000 | 3/2010 | |
| CN | 101688219 | 3/2010 | |
| WO | WO 2007053482 A2 * | 5/2007 | C12N 9/0069 |
| WO | 2011066384 | 6/2011 | |

OTHER PUBLICATIONS

Hohe et al, Plant Cell Rep. (2003) 21:1135-1142.*

GenBank Accession No. AC243160, submitted on Nov. 13, 2010.*

Dow AgroSciences Australia, Risk assessment and risk management plan, DIR 040/2003, Nov. 2003.*

International Search Report and Written Opinion for International Application No. PCT/US2013/022658, dated Jan. 23, 2013.

NCBI, GenBank accession No. FR875178.1 (Jul. 4, 2011).

NCBI, GenBank accession No. AJ506295.1 (Aug. 1, 2007).

NCBI, GenBank accession No. JF806639.1 (Sep. 21, 2011).

NCBI, GenBank accession No. AF019744.1 (Mar. 24, 2003).

NCBI, GenBank accession No. HQ233647.1 (Apr. 9, 2011).

NCBI, GenBank accession No. L05399.1 (Jun. 11, 1993).

Terry R. et al., 'Robust crop resistance to broadleaf and grass herbicides provided by aryloxyalkanoate dioxygenase transgenes' PNAS, Nov. 8, 2011, pp. 20240-20245, vol. 107, No. 47.

* cited by examiner

*Primary Examiner* — Mykola V Kovalenko

(74) *Attorney, Agent, or Firm* — C. Philip Poirier; Magleby Cataxinos & Greenwood

(57) ABSTRACT

Cotton event pDAB4468.18.07.1 comprises genes encoding AAD-12 and PAT, affording herbicide tolerance to cotton crops containing the event, and enabling methods for crop protection.

17 Claims, 2 Drawing Sheets

Plasmid map of pDAB4468.

Schematic diagram of PCR primer locations used to confirm the presence and insertion of cotton event pDAB4468.18.07.1 within the cotton genome.

HERBICIDE TOLERANT COTTON EVENT PDAB4468.18.07.1

CROSS-REFERENCE TO RELATED APPLICATION

This application claims the benefit of U.S. Provisional Patent Application Ser. No. 61/589,602, filed Jan. 23, 2012, the disclosure of which is hereby incorporated herein in its entirety by this reference.

BACKGROUND OF INVENTION

The gene encoding AAD-12 (aryloxyalkanoate dioxygenase-12) is capable of imparting commercial levels of tolerance to the phenoxyacetic acid herbicides, 2,4-D and MCPA, and the pyridyloxyacetic acid herbicides, triclopyr and fluroxypyr, when expressed in transgenic plants. The gene encoding PAT (phosphinothricin acetyltransferase) is capable of imparting tolerance to the herbicide phoshpinothricin (glufosinate) when expressed in transgenic plants. PAT has been successfully expressed in cotton for use both as a selectable marker in producing transgenic crops, and to impart commercial levels of tolerance to the herbicide glufosinate in transgenic plants.

The expression of transgenes in plants is known to be influenced by their location in the plant genome, perhaps due to chromatin structure (e.g., heterochromatin) or the proximity of transcriptional regulatory elements (e.g., enhancers) close to the integration site (Weising et al., *Ann. Rev. Genet* 22:421-477, 1988). At the same time the presence of the transgene at different locations in the genome will influence the overall phenotype of the plant in different ways. For this reason, it is often necessary to screen a large number of transgenic events in order to identify a specific transgenic event characterized by optimal expression of an introduced gene of interest. For example, it has been observed in plants and in other organisms that there may be a wide variation in levels of expression of an introduced gene among events. There may also be differences in spatial or temporal patterns of expression, for example, differences in the relative expression of a transgene in various plant tissues, that may not correspond to the patterns expected from transcriptional regulatory elements present in the introduced gene construct. For this reason, it is common to produce hundreds to thousands of different events and screen those events for a single event that has desired transgene expression levels and patterns for commercial purposes. An event that has desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It is desirable to be able to detect the presence of a particular event in order to determine whether progeny of a sexual cross contain a transgene or group of transgenes of interest. In addition, a method for detecting a particular event would be helpful for complying with regulations requiring the pre-market approval and labeling of food or fiber derived from recombinant crop plants, for example, or for use in environmental monitoring, monitoring traits in crops in the field, or monitoring products derived from a crop harvest, as well as for use in ensuring compliance of parties subject to regulatory or contractual terms.

It is possible to detect the presence of a transgenic event by any nucleic acid detection method known in the art including, but not limited to, the polymerase chain reaction (PCR) or DNA hybridization using nucleic acid probes. These detection methods generally focus on frequently used genetic elements, such as promoters, terminators, marker genes, etc., because for many DNA constructs, the coding region is interchangeable. As a result, such methods may not be useful for discriminating between different events, particularly those produced using the same DNA construct or very similar constructs unless the DNA sequence of the flanking DNA adjacent to the inserted heterologous DNA is known. For example, an event-specific PCR assay is described in United States Patent Application 2006/0070139 for maize event DAS-59122-7. It would be desirable to have a simple and discriminative method for the identification of cotton event pDAB4468.18.07.1.

BRIEF SUMMARY OF THE INVENTION

Embodiments of the present invention relate to a new herbicide tolerant transgenic cotton transformation event, designated as cotton event pDAB4468.18.07.1, comprising aad-12 and pat, as described herein, inserted into a specific site within the genome of a cotton cell. Representative cotton seed has been deposited with American Type Culture Collection (ATCC) ATCC Deposit No. PTA-12456. The DNA of cotton plants containing this event includes the junction/flanking sequences described herein that characterize the location of the inserted DNA within the cotton genome. SEQ ID NO:1 and SEQ ID NO:2 are diagnostic for cotton event pDAB4468.18.07.1. More particularly, sequences surrounding the junctions at bp 2885/2886 of SEQ ID NO:1, and bp 147/148 of SEQ ID NO:2 are diagnostic for cotton event pDAB4468.18.07.1. As exemplified below, sequences comprising these junctions are characteristic of DNA of cotton plants containing cotton event pDAB4468.18.07.1.

In one embodiment, the invention provides a cotton plant, or part thereof, that is tolerant to phenoxyacetic acid herbicides such as 2,4-D and MCPA. In another embodiment, the invention provides a cotton plant, or part thereof, that is tolerant to the pyridyloxyacetic acid herbicides such as triclopyr and fluroxypyr. In an additional embodiment the invention provides a cotton plant that has a genome comprising one or more sequences selected from the group consisting of bp 2867-2906 of SEQ ID NO:1; bp 2837-2936 of SEQ ID NO:1; bp 2787-2986 of SEQ ID NO:1; bp 2737-3036 of SEQ ID NO:1; bp 128-167 of SEQ ID NO:2; bp 98-197 of SEQ ID NO:2; bp 48-247 of SEQ ID NO:2; and bp 1-297 of SEQ ID NO:2, and complements thereof. In another embodiment, the invention provides seed of such plants.

In another embodiment, the invention provides a cotton plant, or part thereof, that is tolerant to compounds that are converted to phenoxyacetate auxin herbicides such as 2,4-D and MCPA (e.g., 2,4-DB, MCPB, etc.). In a further embodiment, the invention provides a cotton plant, or part thereof, that is tolerant to compounds that are converted to pyridyloxyacetic acid herbicides such as triclopyr and fluroxypyr (e.g., triclopyrB, fluroxypyrB, etc.). The butyric acid moiety present in the phenoxyacetate auxin and pyridyloxyacetic acid herbicides is converted through β-oxidation to the phytotoxic form of the herbicides. The butanoic acid forms of the herbicides are themselves nonherbicidal. They are converted to their respective acid form by β-oxidation within susceptible plants (i.e., cotton plants), and it is the acetic acid form of the herbicide that is phytotoxic. Plants incapable of rapid β-oxidation are not harmed by the butanoic acid herbicides. However, plants that are capable of rapid β-oxidation and can convert the butanoic acid herbicide to the acetic form are subsequently protected by AAD-12. Accordingly, the invention provides a cotton plant that has a genome comprising one or more sequences selected from the group consisting of bp 2867-2906 of SEQ ID NO:1; bp 2837-2936 of SEQ ID NO:1; bp 2787-2986 of SEQ ID NO:1; bp 2737-3036 of SEQ ID NO:1; bp 128-167 of SEQ ID NO:2; bp 98-197 of SEQ ID NO:2; bp 48-247 of SEQ ID NO:2; and bp 1-297 of SEQ ID NO:2, and complements thereof. In another embodiment, the invention provides seed of such plants.

In another embodiment, the invention provides a method of controlling weeds in a cotton crop that comprises applying phenoxyacetic acid herbicides such as 2,4-D and MCPA, to the cotton crop, where the cotton crop comprises cotton plants that have a genome containing one or more sequences selected from the group consisting of bp 2867-2906 of SEQ ID NO:1; bp 2837-2936 of SEQ ID NO:1; bp 2787-2986 of SEQ ID NO:1; bp 2737-3036 of SEQ ID NO:1; bp 128-167 of SEQ ID NO:2; bp 98-197 of SEQ ID NO:2; bp 48-247 of SEQ ID NO:2; and bp 1-297 of SEQ ID NO:2, and complements thereof, which are diagnostic for the presence of cotton event pDAB4468.18.07.1. In another embodiment, the invention provides a method of controlling weeds in a cotton crop that comprises applying pyridyloxyacetic acid herbicides, such as triclopyr and fluroxypyr, to the cotton crop, where the cotton crop comprises cotton plants that have a genome containing one or more sequences selected from the group consisting of bp 2867-2906 of SEQ ID NO:1; bp 2837-2936 of SEQ ID NO:1; bp 2787-2986 of SEQ ID NO:1; bp 2737-3036 of SEQ ID NO:1; bp 128-167 of SEQ ID NO:2; bp 98-197 of SEQ ID NO:2; bp 48-247 of SEQ ID NO:2; and bp 1-297 of SEQ ID NO:2, and complements thereof, which are diagnostic for the presence of cotton event pDAB4468.18.07.1. Presence of the aad-12 gene in cotton event pDAB4468.18.07.1 imparts tolerance to phenoxyacetic acid herbicides and pyridyloxyacetic acid herbicides.

In another embodiment, the invention provides a method of controlling weeds in a cotton crop that comprises applying glufosinate herbicide to the cotton crop, said cotton crop comprising cotton plants that have a genome containing one or more sequences selected from the group consisting of bp 2867-2906 of SEQ ID NO:1; bp 2837-2936 of SEQ ID NO:1; bp 2787-2986 of SEQ ID NO:1; bp 2737-3036 of SEQ ID NO:1; bp 128-167 of SEQ ID NO:2; bp 98-197 of SEQ ID NO:2; bp 48-247 of SEQ ID NO:2; and bp 1-297 of SEQ ID NO:2, and complements thereof, which are diagnostic for the presence of cotton event pDAB4468.18.07.1. Presence of the pat gene in cotton event pDAB4468.18.07.1 imparts tolerance to glufosinate herbicide.

In another embodiment, the invention provides a method of detecting cotton event pDAB4468.18.07.1 in a sample comprising cotton DNA, said method comprising:

contacting said sample with a first primer at least 10 bp in length that selectively binds to a flanking sequence within bp 1-2885 of SEQ ID NO:1 or the complement thereof, and a second primer at least 10 bp in length that selectively binds to an insert sequence within bp 2886-3205 of SEQ ID NO:1 or the complement thereof; and assaying for an amplicon generated between said primers; or (b) contacting said sample with a first primer at least 10 bp in length that selectively binds to an insert sequence within bp 1-147 of SEQ ID NO:2 or the complement thereof, and a second primer at least 10 bp in length that selectively binds to a flanking sequence within bp 148-1049 of SEQ ID NO:2 or the complement thereof; and (c) assaying for an amplicon generated between said primers.

In another embodiment, the invention provides a method of detecting cotton event pDAB4468.18.07.1 comprising:

(a) contacting said sample with a first primer that selectively binds to a flanking sequence selected from the group consisting of bp 1-2885 of SEQ ID NO:1 and bp 148-1049 of SEQ ID NO:2, and complements thereof; and a second primer that selectively binds to SEQ ID NO:3, or the complement thereof;

(b) subjecting said sample to polymerase chain reaction; and (c) assaying for an amplicon generated between said primers.

In another embodiment, the invention provides a method of breeding a cotton plant comprising: crossing a first plant with a second cotton plant to produce a third cotton plant, said first plant comprising DNA comprising one or more sequence selected from the group consisting of bp 2867-2906 of SEQ ID NO:1; bp 2837-2936 of SEQ ID NO:1; bp 2787-2986 of SEQ ID NO:1; bp 2737-3036 of SEQ ID NO:1; bp 128-167 of SEQ ID NO:2; bp 98-197 of SEQ ID NO:2; bp 48-247 of SEQ ID NO:2; and bp 1-297 of SEQ ID NO:2, and complements thereof and assaying said third cotton plant for presence of DNA comprising one or more sequences selected from the group consisting of bp 2867-2906 of SEQ ID NO:1; bp 2837-2936 of SEQ ID NO:1; bp 2787-2986 of SEQ ID NO:1; bp 2737-3036 of SEQ ID NO:1; bp 128-167 of SEQ ID NO:2; bp 98-197 of SEQ ID NO:2; bp 48-247 of SEQ ID NO:2; and bp 1-297 of SEQ ID NO:2, and complements thereof.

In another embodiment, the invention provides an isolated DNA molecule that is diagnostic for cotton event pDAB4468.18.07.1. Such molecules include, in addition to SEQ ID NOS: 1 and 2, molecules of at least 40 bp in length which comprise a polynucleotide sequence which spans the bp 2885/2886 junction of SEQ ID NO:1, and molecules of at least 40 bp in length which comprise a polynucleotide sequence which spans the bp 147/148 junction of SEQ ID NO:2. Examples are bp 2867-2906 of SEQ ID NO:1; bp 2837-2936 of SEQ ID NO:1; bp 2787-2986 of SEQ ID NO:1; bp 2737-3036 of SEQ ID NO:1; bp 128-167 of SEQ ID NO:2; bp 98-197 of SEQ ID NO:2; bp 48-247 of SEQ ID NO:2; and bp 1-297 of SEQ ID NO:2, and complements thereof.

In another embodiment, the invention provides cotton fiber, grain, seed, seed oil, or seed meal which comprises cotton event pDAB4468.18.07.1 in said fiber, grain, seed, seed oil, or seed meal as demonstrated by said fiber, grain, seed, seed oil, or seed meal comprising DNA comprising one or more sequences selected from the group consisting bp 2867-2906 of SEQ ID NO:1; bp 2837-2936 of SEQ ID NO:1; bp 2787-2986 of SEQ ID NO:1; bp 2737-3036 of SEQ ID NO:1; bp 128-167 of SEQ ID NO:2; bp 98-197 of SEQ ID NO:2; bp 48-247 of SEQ ID NO:2; and bp 1-297 of SEQ ID NO:2, and complements thereof.

Embodiments of the invention also include cotton plant cells and plant parts including, but not limited to, pollen, ovules, flowers, shoots, roots, and leaves, and nuclei of vegetative cells, pollen cells, seed, seed oil and seed meal, and egg cells, that contain cotton event pDAB4468.18.07.1.

In some embodiments, cotton event pDAB4468.18.07.1 can be combined with other traits, including, for example, other herbicide tolerance gene(s) and/or insect-inhibitory proteins and transcription regulatory sequences (i.e., RNA interference, dsRNA, transcription factors, etc). The additional traits may be stacked into the plant genome via plant breeding, re-transformation of the transgenic plant containing cotton event pDAB4468.18.07.1, or addition of new traits through targeted integration via homologous recombination.

Other embodiments include the excision of polynucleotide sequences which comprise cotton event pDAB4468.18.07.1, including for example, the pat gene expression cassette. Upon excision of a polynucleotide sequence, the modified event may be re-targeted at a specific chromosomal site wherein additional polynucleotide sequences are stacked with cotton event pDAB4468.18.07.1.

In one embodiment, the present invention encompasses a cotton chromosomal target site located on chromosome 26 of the D genome between the flanking sequences set forth in SEQ ID NOS:1 and 2.

In one embodiment, the present invention encompasses a method of making a transgenic cotton plant comprising inserting a heterologous nucleic acid at a position on chromosome 26 of the D genome between the genomic sequences set forth in SEQ ID NOS:1 and 2, i.e., between bp 1-2885 of SEQ ID NO:1 and bp 148-1049 of SEQ ID NO:2.

Additionally, embodiments of the invention also provide assays for detecting the presence of the subject event in a sample (of cotton fibers, for example). The assays can be based on the DNA sequence of the recombinant construct, inserted into the cotton genome, and on the genomic sequences flanking the insertion site. Kits and conditions useful in conducting the assays are also provided.

Embodiments of the invention also relate in part to the cloning and analysis of the DNA sequences of the border regions resulting from insertion of T-DNA from pDAB4468 in transgenic cotton lines. These sequences are unique. Based on the insert and junction sequences, event-specific primers can be and were generated. PCR analysis demonstrated that these events can be identified by analysis of the PCR amplicons generated with these event-specific primer sets. Thus, these and other related procedures can be used to uniquely identify cotton lines comprising the event of the subject invention.

An embodiment provides a method of controlling weeds in a cotton crop that comprises applying phenoxyacetic acid herbicide to the cotton crop, said cotton crop comprising cotton plants comprising DNA that comprises a sequence selected from the group consisting of bp 2867-2906 of SEQ ID NO:1; bp 2837-2936 of SEQ ID NO:1; bp 2787-2986 of SEQ ID NO:1; bp 2737-3036 of SEQ ID NO:1; bp 128-167 of SEQ ID NO:2; bp 98-197 of SEQ ID NO:2; bp 48-247 of SEQ ID NO:2; and bp 1-297 of SEQ ID NO:2. In a further aspect of this method, the phenoxyacetic acid herbicide is 2,4-D. In a further aspect of this method, the phenoxyacetic acid herbicide is MCPA.

An embodiment provides a method of controlling weeds in a cotton crop that comprises applying pyridyloxyacetic acid herbicide to the cotton crop, said cotton crop comprising cotton plants comprising DNA that comprises a sequence selected from the group consisting of bp 2867-2906 of SEQ ID NO:1; bp 2837-2936 of SEQ ID NO:1; bp 2787-2986 of SEQ ID NO:1; bp 2737-3036 of SEQ ID NO:1; bp 128-167 of SEQ ID NO:2; bp 98-197 of SEQ ID NO:2; bp 48-247 of SEQ ID NO:2; and bp 1-297 of SEQ ID NO:2. In a further aspect of this method, the pyridyloxyacetic acid herbicide is triclopyr. In a further aspect of this method, the pyridyloxyacetic acid herbicide is fluroxypyr.

An embodiment provides a method of controlling weeds in a cotton crop that comprises applying glufosinate herbicide to the cotton crop, said cotton crop comprising cotton plants comprising DNA that comprises a sequence selected from the group consisting of bp 2867-2906 of SEQ ID NO:1; bp 2837-2936 of SEQ ID NO:1; bp 2787-2986 of SEQ ID NO:1; bp 2737-3036 of SEQ ID NO:1; bp 128-167 of SEQ ID NO:2; bp 98-197 of SEQ ID NO:2; bp 48-247 of SEQ ID NO:2; and bp 1-297 of SEQ ID NO:2.

An embodiment provides an isolated DNA sequence comprising one or more sequences selected from the group consisting of bp 2867-2906 of SEQ ID NO:1; bp 2837-2936 of SEQ ID NO:1; bp 2787-2986 of SEQ ID NO:1; bp 2737-3036 of SEQ ID NO:1; bp 128-167 of SEQ ID NO:2; bp 98-197 of SEQ ID NO:2; bp 48-247 of SEQ ID NO:2; and bp 1-297 of SEQ ID NO:2.

An embodiment provides a method of breeding a cotton plant comprising: crossing a first plant with a second cotton plant to produce a third cotton plant, said first plant comprising DNA comprising one or more sequences selected from the group consisting of bp 2867-2906 of SEQ ID NO:1; bp 2837-2936 of SEQ ID NO:1; bp 2787-2986 of SEQ ID NO:1; bp 2737-3036 of SEQ ID NO:1; bp 128-167 of SEQ ID NO:2; bp 98-197 of SEQ ID NO:2; bp 48-247 of SEQ ID NO:2; and bp 1-297 of SEQ ID NO:2, and complements thereof; and assaying said third cotton plant for the presence of DNA comprising one or more sequences selected from the group consisting of bp 2867-2906 of SEQ ID NO:1; bp 2837-2936 of SEQ ID NO:1; bp 2787-2986 of SEQ ID NO:1; bp 2737-3036 of SEQ ID NO:1; bp 128-167 of SEQ ID NO:2; bp 98-197 of SEQ ID NO:2; bp 48-247 of SEQ ID NO:2; and bp 1-297 of SEQ ID NO:2, and complements thereof.

An embodiment provides an isolated DNA molecule comprising a junction sequence comprising at least one sequence selected from the group consisting of bp 2867-2906 of SEQ ID NO:1; bp 2837-2936 of SEQ ID NO:1; bp 2787-2986 of SEQ ID NO:1; bp 2737-3036 of SEQ ID NO:1; bp 128-167 of SEQ ID NO:2; bp 98-197 of SEQ ID NO:2; bp 48-247 of SEQ ID NO:2; and bp 1-297 of SEQ ID NO:2, and complements thereof.

An embodiment provides a cotton seed comprising in its genome a DNA sequence selected from the group consisting of residues 2867-2906 of SEQ ID NO:1; residues 2837-2936 of SEQ ID NO:1; residues 2787-2986 of SEQ ID NO:1; residues 2737-3036 of SEQ ID NO:1; residues 128-167 of SEQ ID NO:2; residues 98-197 of SEQ ID NO:2; residues 48-247 of SEQ ID NO:2; and residues 1-297 of SEQ ID NO:2, and complements thereof. A further embodiment provides a cotton seed comprising in its genome AAD-12/PAT cotton event pDAB4468.18.07.1 and having representative cotton seed deposited with American Type Culture Collection under Accession No. PTA-12456. A further embodiment provides a cotton plant produced by growing a cotton seed of either of these two embodiments. A further embodiment provides a cotton seed produced by this cotton plant, wherein said seed comprises in its genome AAD-12/PAT cotton event pDAB4468.18.07.1 as present in a cotton seed deposited with American Type Culture Collection under Accession No. PTA-12456. A further embodiment provides a part of this cotton plant, wherein said part is selected from the group consisting of pollen, ovule, flowers, bolls, shoots, roots, and leaves, and said part comprises AAD-12/PAT cotton event pDAB4468.18.07.1. A further embodiment provides a composition derived from the cotton plant or a part thereof, wherein said composition is a commodity product selected from the group consisting of cotton meal, cotton fiber, and cotton oil.

In a further embodiment, the cotton plant comprises a DNA sequence having at least 95% sequence identity with residues 2,886-9,253 of SEQ ID NO:17. An embodiment provides a progeny cotton plant of the plant of the above embodiment, wherein said plant exhibits tolerance to phenoxyacetic acid, pyridyloxyacetic acid, and glufosinate herbicides, and said tolerance is due to expression of a protein encoded in said event or said genome.

A further embodiment provides a cotton seed comprising a genome comprising a DNA sequence having at least 95% sequence identity with SEQ ID NO:17. A further embodiment provides a plant produced by growing this cotton seed.

An embodiment provides a transgenic cotton plant or part thereof comprising cotton event pDAB4468.18.07.1, wherein representative cotton seeds comprising cotton event pDAB4468.18.07.1 have been deposited with American Type Culture Collection under Accession No. PTA-12456.

SEED DEPOSIT

As part of this disclosure, at least 2500 seeds of a cotton line comprising cotton event pDAB4468.18.07.1 have been deposited and made available to the public without restriction (but subject to patent rights), with the American Type Culture Collection (ATCC), University Boulevard, Manassas, Va., 20110. The deposit, designated as ATCC Deposit No. PTA-12456, was made on behalf of Dow AgroSciences LLC on Jan. 23, 2012. This deposit was made and will be maintained in accordance with and under the terms of the Budapest Treaty with respect to seed deposits for the purposes of patent procedure.

BRIEF DESCRIPTION OF THE SEQUENCES

SEQ ID NO:1 is the 5' DNA flanking border sequence for cotton event pDAB4468.18.07.1. Nucleotides 1-2885 are genomic sequence. Nucleotides 2886-3205 are insert sequence.

SEQ ID NO:2 is the 3' DNA flanking border sequence for cotton event pDAB4468.18.07.1. Nucleotides 1-147 are insert sequence. Nucleotides 148-1049 are genomic sequence.

SEQ ID NO:3 is the T-strand DNA sequence of pDAB4468, which is annotated below in Table 1.

SEQ ID NO:4 is oligonucleotide primer 3endG1 for confirmation of 3' border genomic DNA.

SEQ ID NO:5 is oligonucleotide primer 3endG2 for confirmation of 3' border genomic DNA.

SEQ ID NO:6 is oligonucleotide primer 3endG3 for confirmation of 3' border genomic DNA.

SEQ ID NO:7 is oligonucleotide primer 5endG1 for confirmation of 5' border genomic DNA.

SEQ ID NO:8 is oligonucleotide primer 5endG2 for confirmation of 5' border genomic DNA.

SEQ ID NO:9 is oligonucleotide primer 5endG3 for confirmation of 5' border genomic DNA.

SEQ ID NO:10 is oligonucleotide primer 5endG4 for confirmation of 5' border genomic DNA.

SEQ ID NO:11 is oligonucleotide primer 5endT1 for confirmation of 5' border genomic DNA.

SEQ ID NO:12 is oligonucleotide primer 5endT2 for confirmation of 5' border genomic DNA.

SEQ ID NO:13 is oligonucleotide primer 5endT3 for confirmation of 5' border genomic DNA.

SEQ ID NO:14 is oligonucleotide primer 3endT1 for confirmation of 3' border genomic DNA.

SEQ ID NO:15 is oligonucleotide primer 3endT2 for confirmation of 3' border genomic DNA.

SEQ ID NO:16 is oligonucleotide primer 3endT3 for confirmation of 3' border genomic DNA.

SEQ ID NO:17 is the expected sequence of cotton event pDAB4468.18.07.1, including the 5' genomic flanking sequence, pDAB4468 T-strand insert, and 3' genomic flanking sequence.

DETAILED DESCRIPTION OF THE INVENTION

Figure 1:
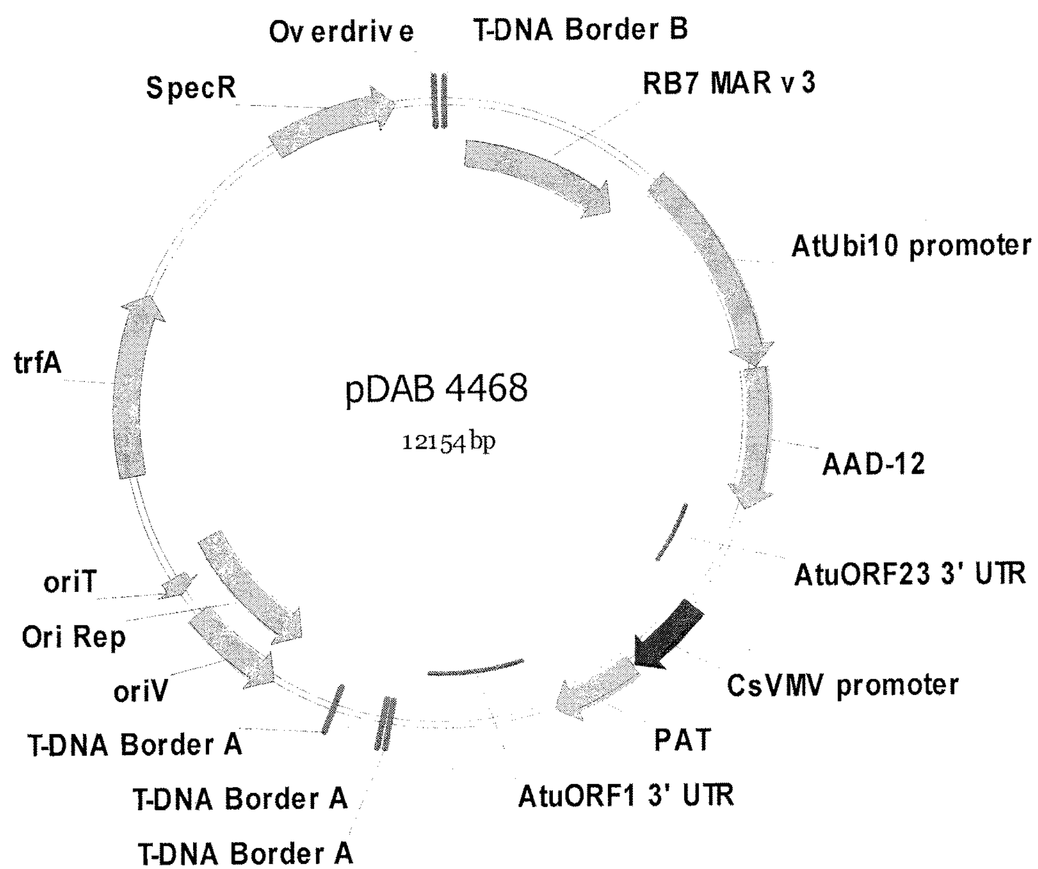
FIG. 1 is a plasmid map of pDAB4468 containing the aad-12 and pat gene expression cassettes.

Both ends of cotton event pDAB4468.18.07.1 insertion have been sequenced and characterized. Event specific assays were developed. The event has also been mapped onto the cotton genome (chromosome 26 of the D genome). The event can be introgressed into further elite lines.

As alluded to above in the Background section, the introduction and integration of a transgene into a plant genome involves some random events (hence the name "event" for a given insertion that is expressed). That is, with many transformation techniques such as *Agrobacterium* transformation, the biolistic transformation (i.e., gene gun), and silicon carbide mediated transformation (i.e., WHISKERS), it is unpredictable where in the genome a transgene will become inserted. Thus, identifying the flanking plant genomic DNA on both sides of the insert is important for identifying a plant that has a given insertion event. For example, PCR primers can be designed that generate a PCR amplicon across the junction region of the insert and the host genome. This PCR amplicon can be used to identify a unique or distinct type of insertion event.

Definitions and examples are provided herein to help describe embodiments of the present invention and to guide those of ordinary skill in the art to practice those embodiments. Unless otherwise noted, terms are to be understood according to conventional usage by those of ordinary skill in the relevant art. The nomenclature for DNA bases as set forth at 37 CFR §1.822 is used.

As used herein, the term "progeny" denotes the offspring of any generation of a parent plant which comprises cotton event pDAB4468.18.07.1.

A transgenic "event" is produced by transformation of plant cells with heterologous DNA, i.e., a nucleic acid construct that includes the transgenes of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that includes the genomic/transgene DNA. Even after repeated back-crossing to a recurrent parent, the inserted transgene DNA and flanking genomic DNA (genomic/transgene DNA) from the transformed parent is present in the progeny of the cross at the same chromosomal location. The term "event" also refers to DNA from the original transformant and progeny thereof comprising the inserted DNA and flanking genomic sequence immediately adjacent to the inserted DNA, which would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

A "junction sequence" or "border sequence" spans the point at which DNA inserted into the genome is linked to DNA from the cotton native genome flanking the insertion point, the identification or detection of one or the other junction sequences in a plant's genetic material being sufficient to be diagnostic for the event. Included are the DNA sequences that span the insertions in herein-described cotton events and similar lengths of flanking DNA. Specific examples of such diagnostic sequences are provided herein; however, other sequences that overlap the junctions of the insertions, or the junctions of the insertions and the genomic sequence, are also diagnostic and could be used in accordance with embodiments of the invention.

Embodiments of the invention relate in part to event identification using such flanking, junction, and insert sequences. Related PCR primers and amplicons are included in embodiments of the invention. In accordance with embodiments of the subject invention, PCR analysis methods using amplicons that span across inserted DNA and its borders can be used to detect or identify commercialized transgenic cotton varieties or lines derived from the subject proprietary transgenic cotton lines.

The flanking/junction sequences are diagnostic for cotton event pDAB4468.18.07.1. Based on these sequences, event-specific primers were generated. PCR analysis demonstrated that these cotton lines can be identified in different cotton genotypes by analysis of the PCR amplicons generated with these event-specific primer sets. Thus, these and other related procedures can be used to uniquely identify these cotton lines. The sequences identified herein are unique.

Detection techniques of embodiments of the subject invention are especially useful in conjunction with plant breeding, to determine which progeny plants comprise a given event, after a parent plant comprising an event of interest is crossed with another plant line in an effort to impart one or more additional traits of interest in the progeny. These PCR analysis methods benefit cotton breeding programs as well as quality control, especially for commercialized transgenic cotton seeds. PCR detection kits for these transgenic cotton lines can also now be made and used. This is also beneficial for product registration and product stewardship.

Furthermore, flanking cotton/genomic sequences can be used to specifically identify the genomic location of each insert. This information can be used to make molecular marker systems specific to each event. These can be used for accelerated breeding strategies and to establish linkage data.

Still further, the flanking sequence information can be used to study and characterize transgene integration processes, genomic integration site characteristics, event sorting, stability of transgenes and their flanking sequences, and gene expression (especially related to gene silencing, transgene methylation patterns, position effects, and potential expression-related elements such as MARS [matrix attachment regions], and the like).

In light of all the subject disclosure, it should be clear that embodiments of the subject invention include seeds available under the ATCC Deposit No. PTA-12456. Embodiments of the invention also include a herbicide-tolerant cotton plant grown from a seed deposited with the ATCC Deposit No. PTA-12456. Embodiments of the invention also include parts of said plant, such as leaves, tissue samples, seeds produced by said plant, pollen, and the like (wherein these parts of the plant comprise aad-12 and pat, and SEQ ID NOS: 1 and 2).

Still further, embodiments of the invention also include descendant and/or progeny plants of plants grown from the deposited seed, preferably a herbicide-resistant cotton plant wherein said plant has a genome comprising a detectable junction/flanking sequence as described herein. As used herein, the term "cotton" means *Gossypium hirsutum* and includes all varieties thereof that can be bred with a cotton plant.

An herbicide tolerant cotton plant of an embodiment of the invention can be bred by first sexually crossing a first parental cotton plant consisting of a cotton plant grown from seed of any one of the lines referred to herein, and a second parental cotton plant, thereby producing a plurality of first progeny plants; then selecting a first progeny plant that is resistant to glufosinate; selfing the first progeny plant, thereby producing a plurality of second progeny plants; and then selecting from the second progeny plants a plant that is resistant to glufosinate. These steps can further include the back-crossing of the first progeny plant or the second progeny plant to the second parental cotton plant or a third parental cotton plant. A cotton crop comprising cotton seeds of an embodiment of the invention, or progeny thereof, can then be planted.

It is also to be understood that two different transgenic plants can also be mated to produce offspring that contain two independently segregating, added, exogenous genes. Selfing of appropriate progeny can produce plants that are homozygous for both added, exogenous genes. Back-crossing to a parental plant and out-crossing with a non-transgenic plant are also contemplated, as is vegetative propagation. Other breeding methods commonly used for different traits and crops are known in the art. Backcross breeding has been used to transfer genes for a simply inherited, highly heritable trait into a desirable homozygous cultivar, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (back-crossed) to the recurrent parent. The resulting plant is expected to have the attributes of the recurrent parent (e.g., cultivar) and the desirable trait transferred from the donor parent.

Likewise an herbicide tolerant cotton plant of an embodiment of the invention can be transformed with additional transgenes using methods known in the art. Transformation techniques such as *Agrobacterium* transformation, the biolistic transformation (i.e., gene gun), and silicon carbide mediated transformation (i.e., WHISKERS), can be used to introduced additional trangene(s) into the genome of cotton event pDAB4468.18.07.1. Selection and characterization of transgenic plants containing the newly inserted transgenes can be completed to identify plants which contain a stable integrant of the novel transgene in addition to the aad-12 and pat genes of embodiments of the invention.

The DNA molecules of embodiments of the present invention can be used as molecular markers in a marker assisted breeding (MAB) method. DNA molecules of embodiments of the present invention can be used in methods (such as, AFLP markers, RFLP markers, RAPD markers, SNPs, and SSRs) that identify genetically linked agronomically useful traits, as is known in the art. The herbicide tolerance traits can be tracked in the progeny of a cross with a cotton plant of embodiments of the subject invention (or progeny thereof and any other cotton cultivar or variety) using the MAB methods. The DNA molecules are markers for this trait, and MAB methods that are well known in the art can be used to track the herbicide tolerance trait(s) in cotton plants where at least one cotton line of embodiments of the subject invention, or progeny thereof, was a parent or ancestor. The methods of embodiments of the present invention can be used to identify any cotton variety having the subject event.

Methods of embodiments of the subject invention include a method of producing an herbicide tolerant cotton plant wherein said method comprises breeding with a plant of an embodiment of the subject invention. More specifically, said methods can comprise crossing two plants of embodiments of the subject invention, or one plant of an embodiment of the subject invention and any other plant. Preferred methods further comprise selecting progeny of said cross by analyzing said progeny for an event detectable in accordance with an embodiment of the subject invention and favorable varietal performance (e.g., yield). For example, embodiments of the subject invention can be used to track the subject event through breeding cycles with plants comprising other desirable traits, such as agronomic traits, disease tolerance or resistance, nematode tolerance or resistance and maturity date. Plants comprising the subject event and the desired trait can be detected, identified, selected, and quickly used in further rounds of breeding, for example. The subject event/trait can also be combined through breeding, and tracked according to embodiments of the subject invention, with further insect resistant trait(s) and/or with further herbicide tolerance traits. Embodiments of the latter are plants comprising the subject event combined with the cry1F and cry1Ac genes, which confer resistance to *Pseudoplusia includens* (soybean looper), *Anticarsia gemmatalis* (velvetbean caterpillar), *Epinotia aporema, Omoides indicatus, Rachiplusia nu, Spodoptera frugiperda, Spodoptera cosmoides, Spodoptera eridania, Heliothis virescens, Heliocoverpa zea, Spilosoma virginica* and *Elasmopalpus lignosellus*, or with a gene encoding resistance to the herbicide dicamba.

Thus, embodiments of the subject invention can be combined with, for example, traits encoding glyphosate resistance (e.g., resistant plant or bacterial EPSPS, GOX, GAT), glufosinate resistance (e.g., dsm-2, bar), acetolactate synthase (ALS)-inhibiting herbicide resistance (e.g., imidazolinones [such as imazethapyr], sulfonylureas, triazolopyrimidine sulfonanilide, pyrmidinylthiobenzoates, and other chemistries [Csr1, SurA, et al.]), bromoxynil resistance (e.g., Bxn), resistance to inhibitors of HPPD (4-hydroxlphenyl-pyruvate-dioxygenase) enzyme, resistance to inhibitors of phytoene desaturase (PDS), resistance to photosystem II inhibiting herbicides (e.g., psbA), resistance to photosystem I inhibiting herbicides, resistance to protoporphyrinogen oxidase IX (PPO)-inhibiting herbicides (e.g., PPO-1), resistance to phenylurea herbicides (e.g., CYP76B1), dicamba-degrading enzymes (see, e.g., US 20030135879), and others could be stacked alone or in multiple combinations to provide the ability to effectively control or prevent weed shifts and/or resistance to any herbicide of the aforementioned classes.

Additionally, cotton event pDAB4468.18.07.1 can be combined with one or more additional input (e.g., insect resistance, pathogen resistance, or stress tolerance, et al.) or output (e.g., increased yield, improved oil profile, improved fiber quality, et al.) traits. Thus, embodiments of the subject invention can be used to provide a complete agronomic package of improved crop quality with the ability to flexibly and cost effectively control any number of agronomic pests.

Methods to integrate a polynucleotide sequence within a specific chromosomal site of a plant cell via homologous recombination have been described within the art. For instance, site specific integration as described in US Patent Application Publication No. 2009/0111188 A1, herein incorporated by reference, describes the use of recombinases or integrases to mediate the introduction of a donor polynucleotide sequence into a chromosomal target. In addition, International Patent Application No. WO 2008/021207, herein incorporated by reference, describes zinc finger mediated-homologous recombination to integrate one or more donor polynucleotide sequences within specific locations of the genome. The use of recombinases such as FLP/FRT as described in U.S. Pat. No. 6,720,475, herein incorporated by reference, or CRE/LOX as described in U.S. Pat. No. 5,658,772, herein incorporated by reference, can be utilized to integrate a polynucleotide sequence into a specific chromosomal site. Finally the use of meganucleases for targeting donor polynucleotides into a specific chromosomal location was described in Puchta et al., PNAS USA 93 (1996) pp. 5055-5060.

Other methods for site specific integration within plant cells are generally known and applicable (Kumar et al., *Trends in Plant Sci.* 6(4) (2001) pp. 155-159). Furthermore, site-specific recombination systems which have been identified in several prokaryotic and lower eukaryotic organisms may be applied to use in plants. Examples of such systems include, but are not limited to: the R/RS recombinase system from the pSR1 plasmid of the yeast *Zygosaccharomyces rouxii* (Araki et al., (1985) J. Mol. Biol. 182: 191-203), and the Gin/gix system of phage Mu (Maeser and Kahlmann (1991) Mol. Gen. Genet. 230: 170-176).

In some embodiments of the present invention, it is desirable to integrate or stack a new transgene(s) in proximity to an existing transgenic event. The transgenic event can be considered a preferred genomic locus which was selected based on unique characteristics such as single insertion site, normal Mendelian segregation and stable expression, and a superior combination of efficacy, including herbicide tolerance and agronomic performance in and across multiple environmental locations. The newly integrated transgenes should maintain the transgene expression characteristics of the existing transformants. Moreover, the development of assays for the detection and confirmation of the newly integrated event would be overcome as the genomic flanking sequences and chromosomal location of the newly integrated event are already identified. Finally, the integration of a new transgene into a specific chromosomal location which is linked to an existing transgene would expedite the introgression of the transgenes into other genetic backgrounds by sexual out-crossing using conventional breeding methods.

In some embodiments of the present invention, it is desirable to excise polynucleotide sequences from a transgenic event. For instance, transgene excision as described in US Patent Application Publication No. 2011/0191877, herein incorporated by reference, employs zinc finger nucleases to remove a polynucleotide sequence, consisting of a gene expression cassette, from a chromosomally integrated transgenic event. The polynucleotide sequence which is removed can be a selectable marker. Upon excision and removal of a polynucleotide sequence the modified transgenic event can be retargeted by the insertion of a polynucleotide sequence. The excision of a polynucleotide sequence and subsequent retargeting of the modified transgenic event provides advantages such as re-use of a selectable marker or the ability to overcome unintended changes to the plant transcriptome which results from the expression of specific genes.

A specific site on chromosome 26 of the D genome within the cotton genome that is excellent for insertion of heterologous nucleic acids is disclosed herein. Thus, embodiments of the subject invention provide methods to introduce heterologous nucleic acids of interest into this pre-established target site or in the vicinity of this target site. Embodiments of the subject invention also encompass a cotton seed and/or a cotton plant comprising any heterologous nucleotide sequence inserted at the disclosed target site or into the general vicinity of such site. One option to accomplish such targeted integration is to excise and/or substitute a different insert in place of the pat expression cassette exemplified herein. In this regard, targeted homologous recombination, for example and without limitation, can be used in accordance with embodiments of the subject invention.

As used herein gene, event or trait "stacking" refers to the combining of desired traits into one transgenic line. Plant breeders stack transgenic traits by making crosses between parents that each have a desired trait and then identifying offspring that have both of these desired traits. Another way to stack genes is by transferring two or more genes into the cell nucleus of a plant at the same time during transformation. Another way to stack genes is by re-transforming a transgenic plant with another gene of interest. For example, gene stacking can be used to combine two or more different traits, including for example, two or more different insect traits, insect resistance trait(s) and disease resistance trait(s), two or more herbicide resistance traits, and/or insect resistance trait(s) and herbicide resistant trait(s). The use of a selectable marker in addition to a gene of interest can also be considered gene stacking.

"Homologous recombination" refers to a reaction between any pair of nucleotide sequences having corresponding sites containing a similar nucleotide sequence through which the two nucleotide sequences can interact (recombine) to form a new, recombinant DNA sequence. The sites of similar nucleotide sequence are each referred to herein as a "homology sequence." Generally, the frequency of homologous recombination increases as the length of the homology sequence increases. Thus, while homologous recombination can occur between two nucleotide sequences that are less than identical, the recombination frequency (or efficiency) declines as the divergence between the two sequences increases. Recombination may be accomplished using one homology sequence on each of the donor and target molecules, thereby generating a "single-crossover" recombination product. Alternatively, two homology sequences may be placed on each of the target and donor nucleotide sequences. Recombination between two homology sequences on the donor with two homology sequences on the target generates a "double-crossover" recombination product. If the homology sequences on the donor molecule flank a sequence that is to be manipulated (e.g., a sequence of interest), the double-crossover recombination with the target molecule will result in a recombination product wherein the sequence of interest replaces a DNA sequence that was originally between the homology sequences on the target molecule. The exchange of DNA sequence between the target and donor through a double-crossover recombination event is termed "sequence replacement."

A preferred plant, or a seed, of embodiments of the subject invention comprises in its genome operative aad-12 and pat nucleotide sequences, as identified herein, together with at least 20-500 or more contiguous flanking nucleotides on both sides of the insert, as identified herein. Unless indicated otherwise, reference to flanking sequences refers to those identified with respect to SEQ ID NOS: 1 and 2. All or part of these flanking sequences could be expected to be transferred to progeny that receive the inserted DNA as a result of a sexual cross of a parental line that includes the event.

Embodiments of the subject invention include tissue cultures of regenerable cells of a plant of an embodiment of the subject invention. Also included is a plant regenerated from such tissue culture, particularly where said plant is capable of expressing all the morphological and physiological properties of an exemplified variety. Preferred plants of embodiments of the subject invention have all the physiological and morphological characteristics of a plant grown from the deposited seed. Embodiments of this invention further comprise progeny of such seed and seed possessing the quality traits of interest.

As used herein, a "line" is a group of plants that display little or no genetic variation between individuals for at least one trait. Such lines may be created by several generations of self-pollination and selection, or vegetative propagation from a single parent using tissue or cell culture techniques.

As used herein, the terms "cultivar" and "variety" are synonymous and refer to a line which is used for commercial production.

"Stability" or "stable" means that with respect to the given component, the component is maintained from generation to generation and, preferably, for at least three generations.

"Commercial Utility" is defined as having good plant vigor and high fertility, such that the crop can be produced by farmers using conventional farming equipment, and the oil with the described components can be extracted from the seed using conventional crushing and extraction equipment.

"Agronomically elite" means that a line has desirable agronomic characteristics such as yield, maturity, disease resistance, and the like, in addition to the herbicide tolerance due to the subject event(s). Any and all of these agronomic characteristics and data points can be used to identify such plants, either as a point or at either end or both ends of a range of characteristics used to define such plants.

As one skilled in the art will recognize in light of this disclosure, preferred embodiments of detection kits, for example, can include probes and/or primers directed to and/or comprising "junction sequences" or "transition sequences" (where the cotton genomic flanking sequence meets the insert sequence). For example, this includes polynucleotide probes, primers, and/or amplicons designed to identify one or both junction sequences (where the insert meets the flanking sequence). One common design is to have one primer that hybridizes in the flanking region, and one primer that hybridizes in the insert. Such primers are often each about at least ~15 residues in length. With this arrangement, the primers can be used to generate/amplify a detectable amplicon that indicates the presence of an event of an embodiment of the subject invention. These primers can be used to generate an amplicon that spans (and includes) a junction sequence as indicated above.

The primer(s) "touching down" in the flanking sequence is typically not designed to hybridize beyond about 1200 bases or so beyond the junction. Thus, typical flanking primers would be designed to comprise at least 15 residues of either strand within 1200 bases into the flanking sequences from the beginning of the insert. That is, primers comprising a sequence of an appropriate size from (or hybridizing to) base pairs 2000-3205 of SEQ ID NO:1 and/or base pairs 1-1049 of SEQ ID NO:2 are within the scope of embodiments of the subject invention. Insert primers can likewise be designed anywhere on the insert, but base pairs 1-6368 of SEQ ID NO:3, can be used, for example, non-exclusively for such primer design.

One skilled in the art will also recognize that primers and probes can be designed to hybridize, under a range of standard hybridization and/or PCR conditions wherein the primer or probe is not perfectly complementary to the exemplified sequence. That is, some degree of mismatch or degeneracy can be tolerated. For an approximately 20 nucleotide primer, for example, typically one or two or so nucleotides do not need to bind with the opposite strand if the mismatched base is internal or on the end of the primer that is opposite the amplicon. Various appropriate hybridization conditions are provided below. Synthetic nucleotide analogs, such as inosine, can also be used in probes. Peptide nucleic acid (PNA) probes, as well as DNA and RNA probes, can also be used. What is important is that such probes and primers are diagnostic for (able to uniquely identify and distinguish) the presence of an event of an embodiment of the subject invention.

It should be noted that errors in PCR amplification can occur which might result in minor sequencing errors, for example. That is, unless otherwise indicated, the sequences listed herein were determined by generating long amplicons from cotton genomic DNAs, and then cloning and sequencing the amplicons. It is not unusual to find slight differences and minor discrepancies in sequences generated and determined in this manner, given the many rounds of amplification that are necessary to generate enough amplicon for sequencing from genomic DNAs. One skilled in the art should recognize and be put on notice that any adjustments needed due to these types of common sequencing errors or discrepancies are within the scope of embodiments of the subject invention.

It should also be noted that it is not uncommon for some genomic sequence to be deleted, for example, when a sequence is inserted during the creation of an event. Thus, some differences can also appear between the subject flanking sequences and genomic sequences listed in GENBANK, for example.

Components of the DNA sequence “insert” are illustrated in the Figures and are discussed in more detail below in the Examples. The DNA polynucleotide sequences of these components, or fragments thereof, can be used as DNA primers or probes in the methods of embodiments of the present invention.

In some embodiments of the invention, compositions and methods are provided for detecting the presence of the transgene/genomic insertion region, in plants and seeds and the like, from a cotton plant. DNA sequences are provided that comprise the subject 5' transgene/genomic insertion region junction sequence provided herein (between base pairs 2885/2886 of SEQ ID NO:1), segments thereof, and complements of the exemplified sequences and any segments thereof. DNA sequences are provided that comprise the subject 3' transgene/genomic insertion region junction sequence provided herein (between base pairs 147/148 of SEQ ID NO:2), segments thereof, and complements of the exemplified sequences and any segments thereof. The insertion region junction sequence spans the junction between heterologous DNA inserted into the genome and the DNA from the cotton cell flanking the insertion site. Such sequences can be diagnostic for the given event.

Based on these insert and border sequences, event-specific primers can be generated. PCR analysis demonstrated that cotton lines of embodiments of the subject invention can be identified in different cotton genotypes by analysis of the PCR amplicons generated with these event-specific primer sets. These and other related procedures can be used to uniquely identify these cotton lines. Thus, PCR amplicons derived from such primer pairs are unique and can be used to identify these cotton lines.

In some embodiments, DNA sequences that comprise a contiguous fragment of the novel transgene/genomic insertion region are an aspect of this invention. Included are DNA sequences that comprise a sufficient length of polynucleotides of transgene insert sequence and a sufficient length of polynucleotides of cotton genomic sequence from one or more of the aforementioned cotton plants and/or sequences that are useful as primer sequences for the production of an amplicon product diagnostic for one or more of these cotton plants.

Related embodiments pertain to DNA sequences that comprise at least 10, 11, 12, 13, 14, 15, 16, 17, 18, 19, 20, 21, 22, 23, 24, 25, or more contiguous nucleotides of a transgene portion of a DNA sequence identified herein (such as SEQ ID NO:1 and segments thereof), or complements thereof, and a similar length of flanking cotton DNA sequence from these sequences, or complements thereof. Such sequences are useful as DNA primers in DNA amplification methods. The amplicons produced using these primers are diagnostic for any of the cotton events referred to herein. Therefore, embodiments of the invention also include the amplicons produced by such DNA primers.

Embodiments of this invention also include methods of detecting the presence of DNA, in a sample, that corresponds to the cotton event referred to herein. Such methods can comprise: (a) contacting the sample comprising DNA with a primer set that, when used in a nucleic acid amplification reaction with DNA from at least one of these cotton event, produces an amplicon that is diagnostic for said event(s); (b) performing a nucleic acid amplification reaction, thereby producing the amplicon; and (c) detecting the amplicon.

Further detection methods of embodiments of the subject invention include a method of detecting the presence of a DNA, in a sample, corresponding to said event, wherein said method comprises: (a) contacting the sample comprising DNA with a probe that hybridizes under stringent hybridization conditions with DNA from said cotton event and which does not hybridize under the stringent hybridization conditions with a control cotton plant (non-event-of-interest DNA); (b) subjecting the sample and probe to stringent hybridization conditions; and (c) detecting hybridization of the probe to the DNA.

In still further embodiments, the subject invention includes methods of producing a cotton plant comprising cotton event pDAB4468.18.07.1 of an embodiment of the subject invention, wherein said method comprises the steps of: (a) sexually crossing a first parental cotton line (comprising an expression cassette of an embodiment of the present invention, which confers 2,4-D and glufosinate tolerance to plants of said line) and a second parental cotton line (that lacks these herbicide tolerance traits) thereby producing a plurality of progeny plants; and (b) selecting a progeny plant by the use of molecular markers. Such methods may optionally comprise the further step of back-crossing the progeny plant to the second parental cotton line to producing a true-breeding cotton plant that comprises the herbicide tolerant traits.

According to another aspect of the invention, methods of determining the zygosity of progeny of a cross with said event is provided. Said methods can comprise contacting a sample, comprising cotton DNA, with a primer set of an embodiment of the subject invention. Said primers, when used in a nucleic-acid amplification reaction with genomic DNA from said cotton events, produce a first amplicon that is diagnostic for said cotton event. Such methods further comprise performing a nucleic acid amplification reaction, thereby producing the first amplicon; detecting the first amplicon; and contacting the sample comprising cotton DNA with a second primer set (said second primer set, when used in a nucleic-acid amplification reaction with genomic DNA from cotton plants, produces a second amplicon comprising an endogenous sequence of the native cotton genomic DNA that does not contain the polynucleotide sequence of said event); and performing a nucleic acid amplification reaction, thereby producing the second amplicon. The methods further comprise detecting the second amplicon, and comparing the first and second amplicons in a sample, wherein the presence of both amplicons indicates the zygosity of the transgene insertion.

DNA detection kits can be developed using the compositions disclosed herein and methods well known in the art of DNA detection. The kits are useful for identification of the subject cotton event DNA in a sample and can be applied to methods for breeding cotton plants containing this DNA. The kits contain DNA sequences complementary to the amplicons, for example, disclosed herein, or to DNA sequences complementary to DNA contained in the transgene genetic elements of the subject events. These DNA sequences can be used in DNA amplification reactions or as probes in a DNA hybridization method. The kits may also contain the reagents and materials necessary for the performance of the detection method.

A "probe" is an isolated nucleic acid molecule to which is attached a conventional detectable label or reporter molecule (such as a radioactive isotope, ligand, chemiluminescent agent, or enzyme). Such a probe can hybridize to a strand of a target nucleic acid, in the case of embodiments of the present invention, to a strand of genomic DNA from one of said cotton events, whether from a cotton plant or from a sample that includes DNA from the event. Probes in accordance with embodiments of the present invention include not only deoxyribonucleic or ribonucleic acids but also polyamides and other probe materials that bind specifically to a target DNA sequence and can be used to detect the presence of that target DNA sequence.

"Primers" are isolated/synthesized nucleic acids that are annealed to a target DNA strand by nucleic acid hybridization to form a hybrid between the primer and the target DNA strand, then extended along the target DNA strand by a polymerase, e.g., a DNA polymerase. Primer pairs of embodiments of the present invention refer to their use for amplification of a target nucleic acid sequence, e.g., by the polymerase chain reaction (PCR) or other conventional nucleic-acid amplification methods.

Probes and primers are generally 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, or 1000, or 2000, or 5000 polynucleotides or more in length. Such probes and primers hybridize specifically to a target sequence under stringent hybridization conditions. Preferably, probes and primers in accordance with embodiments of the present invention have complete sequence similarity with the target sequence, although probes differing from the target sequence and that retain the ability to hybridize to target sequences may be designed by conventional methods.

Methods for preparing and using probes and primers are described, for example, in Molecular Cloning: A Laboratory Manual, 2nd ed., vol. 1-3, ed. Sambrook et al., Cold Spring Harbor Laboratory Press, Cold Spring Harbor, N.Y., 1989. PCR-primer pairs can be derived from a known sequence, for example, by using computer programs intended for that purpose.

Primers and probes based on the flanking DNA and insert sequences disclosed herein can be used to confirm (and, if necessary, to correct) the disclosed sequences by conventional methods, e.g., by re-cloning and sequencing such sequences.

The nucleic acid probes and primers of embodiments of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Molecules that exhibit complete complementarity will generally hybridize to one another with sufficient stability to permit them to remain annealed to one another under conventional "high-stringency" conditions. Conventional high-stringency conditions are described by Sambrook et al., 1989.

Two molecules are said to exhibit "minimal complementarity" if they can hybridize to one another with sufficient stability to permit them to remain annealed to one another under at least conventional "low-stringency" conditions. Conventional low-stringency conditions are described by Sambrook et al., 1989. In order for a nucleic acid molecule to serve as a primer or probe it need only exhibit minimal complementarity of sequence to be able to form a stable double-stranded structure under the particular solvent and salt concentrations employed.

The term "stringent condition" or "stringency conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52 and 9.56-9.58.

Depending on the application envisioned, one can use varying conditions of stringent conditions or polynucleotide sequence degeneracy of a probe or primer to achieve varying degrees of selectivity of hybridization towards the target sequence. For applications requiring high selectivity, one will typically employ relatively stringent conditions for hybridization of one polynucleotide sequence with a second polynucleotide sequence, e.g., one will select relatively low salt and/or high temperature conditions, such as provided by about 0.02 M to about 0.15 M NaCl at temperatures of about 50° C. to about 70° C. Stringent conditions, for example, could involve washing the hybridization filter at least twice with high-stringency wash buffer (0.2×SSC, 0.1% SDS, 65° C.). Appropriate stringency conditions which promote DNA hybridization, for example, 6.0× sodium chloride/sodium citrate (SSC) at about 45 C, followed by a wash of 2.0×SSC at 50° C. are known to those skilled in the art. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little, if any, mismatch between the probe and the template or target strand. Detection of DNA sequences via hybridization is well-known to those of skill in the art, and the teachings of U.S. Pat. Nos. 4,965,188 and 5,176,995 are exemplary of the methods of hybridization analyses.

In a particularly preferred embodiment, a nucleic acid of an embodiment of the present invention will specifically hybridize to one or more of the primers (or amplicons or other sequences) exemplified or suggested herein, including complements and fragments thereof, under high stringency conditions. In one aspect of the present invention, a marker nucleic acid molecule of an embodiment of the present invention has the nucleic acid sequence as set forth herein in one of the exemplified sequences, or complements and/or fragments thereof.

In another aspect of the present invention, a marker nucleic acid molecule of an embodiment of the present invention shares between 80% and 100% or 90% and 100% sequence identity with such nucleic acid sequences. In a further aspect of the present invention, a marker nucleic acid molecule of an embodiment of the present invention shares between 95% and 100% sequence identity with such sequence. Such sequences may be used as markers in plant breeding methods to identify the progeny of genetic crosses. The hybridization of the probe to the target DNA molecule can be detected by any number of methods known to those skilled in the art; these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic-acid amplification of a target nucleic acid sequence that is part of a nucleic acid template. For example, to determine whether the cotton plant resulting from a sexual cross contains transgenic event genomic DNA from the cotton plant of an embodiment of the present invention, DNA extracted from a cotton plant tissue sample may be subjected to nucleic acid amplification method using a primer pair that includes a primer derived from flanking sequence in the genome of the plant adjacent to the insertion site of inserted heterologous DNA, and a second primer derived from the inserted heterologous DNA to produce an amplicon that is diagnostic for the presence of the event DNA. The amplicon is of a length and has a sequence that is also diagnostic for the event. The amplicon may range in length from the combined length of the primer pairs plus one nucleotide base pair, and/or the combined length of the primer pairs plus about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500, 750, 1000, 1250, 1500, 1750, 2000, or more nucleotide base pairs (plus or minus any of the increments listed above). Alternatively, a primer pair can be derived from flanking sequence on both sides of the inserted DNA so as to produce an amplicon that includes the entire insert nucleotide sequence. A member of a primer pair derived from the plant genomic sequence may be located a distance from the inserted DNA sequence. This distance can range from one nucleotide base pair up to about twenty thousand nucleotide base pairs. The use of the term "amplicon" specifically excludes primer dimers that may be formed in the DNA thermal amplification reaction.

Nucleic-acid amplification can be accomplished by any of the various nucleic-acid amplification methods known in the art, including the polymerase chain reaction (PCR). A variety of amplification methods are known in the art and are described, inter alia, in U.S. Pat. No. 4,683,195 and U.S. Pat. No. 4,683,202. PCR amplification methods have been developed to amplify up to 22 kb of genomic DNA. These methods as well as other methods known in the art of DNA amplification may be used in the practice of embodiments of the present invention. The sequence of the heterologous transgene DNA insert or flanking genomic sequence from a subject cotton event can be verified (and corrected if necessary) by amplifying such sequences from the event using primers derived from the sequences provided herein followed by standard DNA sequencing of the PCR amplicon or of the cloned DNA.

The amplicon produced by these methods may be detected by a plurality of techniques. Agarose gel electrophoresis and staining with ethidium bromide is a common well-known method of detecting DNA amplicons. Another such method is Genetic Bit Analysis, where an DNA oligonucleotide is designed which overlaps both the adjacent flanking genomic DNA sequence and the inserted DNA sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labeled ddNTPs specific for the expected next base. Analysis of a bound product can be completed via quantitating the amount of fluorescent signal. A fluorescent signal indicates presence of the insert/flanking sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is designed to hybridize to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal that is measured. A light signal indicates the presence of the transgene insert/flanking sequence due to successful amplification, hybridization, and single or multi-base extension.

Fluorescence Polarization is another method that can be used to detect an amplicon of an embodiment of the present invention. Following this method, an oligonucleotide is designed which overlaps the genomic flanking and inserted DNA junction. The oligonucleotide is hybridized to the single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation of the fluorescently labeled ddNTP can be measured as a change in polarization using a fluorometer. A change in polarization indicates the presence of the transgene insert/flanking sequence due to successful amplification, hybridization, and single base extension.

TAQMAN® (PE Applied Biosystems, Foster City, Calif.) is a method of detecting and quantifying the presence of a DNA sequence. Briefly, a FRET oligonucleotide probe is designed that overlaps the genomic flanking and insert DNA junction. The FRET probe and PCR primers (one primer in the insert DNA sequence and one in the flanking genomic sequence) are cycled in the presence of a thermostable polymerase and dNTPs. During specific amplification, the Taq DNA polymerase proofreading mechanism releases the fluorescent moiety away from the quenching moiety on the FRET probe. A fluorescent signal indicates the presence of the flanking/transgene insert sequence due to successful amplification and hybridization.

Molecular Beacons have been described for use in polynucleotide sequence detection. Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking genomic/transgene insert sequence due to successful amplification and hybridization.

Having disclosed a location in the cotton genome that is excellent for an insertion, embodiments of the subject invention also comprise a cotton seed and/or a cotton plant comprising at least one non-cotton event pDAB4468.18.07.1 insert in the general vicinity of this genomic location. One option is to substitute a different insert in place of the one from cotton event pDAB4468.18.07.1 exemplified herein. In general, targeted homologous recombination, for example, is employed in particular embodiments. This type of technology is the subject of, for example, WO 03/080809 A2 and the corresponding published U.S. application (US 20030232410). Thus, embodiments of the subject invention include plants and plant cells comprising a heterologous insert (in place of or with multi-copies of the aad-12 or pat genes), flanked by all or a recognizable part of the flanking sequences identified herein (bp 1-2885 of SEQ ID NO:1 and bp 148-1049 of SEQ ID NO:2). An additional copy (or additional copies) of a aad-12 or pat gene could also be targeted for insertion in this/these manner(s).

All patents, patent applications, provisional applications, and publications referred to or cited herein are incorporated by reference in their entirety to the extent they are not inconsistent with the explicit teachings of this specification. The following examples are included to illustrate procedures for practicing embodiments of the invention and to demonstrate certain preferred embodiments of the invention. These examples should not be construed as limiting. It should be appreciated by those of skill in the art that the techniques disclosed in the following examples represent specific approaches used to illustrate preferred modes for its practice. However, those of skill in the art should, in light of the present disclosure, appreciate that many changes can be made in these specific embodiments while still obtaining like or similar results without departing from the spirit and scope of the invention. Unless otherwise indicated, all percentages are by weight and all solvent mixture proportions are by volume unless otherwise noted.

The following abbreviations are used unless otherwise indicated.

bp base pair
° C. degrees Celsius
DNA deoxyribonucleic acid
EDTA ethylenediaminetetraacetic acid
kb kilobase
μg microgram
μL microliter
mL milliliter
M molar mass
PCR polymerase chain reaction
PTU plant transcription unit or expression cassette
SDS sodium dodecyl sulfate
SSC a buffer solution containing a mixture of sodium chloride and sodium citrate, pH 7.0
TBE a buffer solution containing a mixture of Tris base, boric acid and EDTA, pH 8.3

EXAMPLES

Example 1: Transformation and Selection of the aad-12 and Pat Cotton Event pDAB4468.18.07.1

Transgenic cotton (*Gossypium hirsutum*) containing the cotton event pDAB4468.18.07.1 was generated through *Agrobacterium*-mediated transformation and selected using medium containing glufosinate. The disarmed *Agrobacterium* strain EHA101 (Hood et al., 1993), carrying the binary vector pDAB4468 (FIG. 1) containing the selectable marker, pat, and the gene of interest, aad-12, within the T-strand DNA region, was used to initiate transformation of cotton plant variety, Coker 310. The DNA T-strand sequence for pDAB4468 is given in SEQ ID NO:3, and is annotated below in Table 1.

TABLE 1

Gene elements located on pDAB4468.

| bp (SEQ ID NO: 3) | Construct element | Reference |
|---|---|---|
| 139-1,304 bp | RB7 MAR v3 | Thompson et al., 1997, WO9727207 |
| 1,400-2,721 bp | AtUbi10 Promoter | Callis, et al., (1990) *J. Biol. Chem.*, 265: 12486-12493 |
| 2,730-3,611 bp | AAD-12 | WO 2007/053482 |
| 3,714-4,170 bp | ORF23 3'UTR | U.S. Pat. No. 5,428,147 |
| 4,285-4,801 bp | CsVMV Promoter | Verdaguer et al., (1996) *Plant Mol. Biol.*, 31: 1129-1139 |
| 4,809-5,360 bp | PAT | Wohlleben et al., (1988) *Gene* 70: 25-37 |
| 5,463-6,166 bp | ORF1 3'UTR | Huang et al., (1990) *J. Bacteriol.* 172: 1814-1822 |

Example 2: Characterization of AAD-12 Protein from Cotton Event pDAB4468.18.07.1

The biochemical properties of the recombinant AAD-12 protein derived from the transgenic cotton event pDAB4468.18.07.1 were characterized. Quantitative enzyme-linked immunosorbent assay (ELISA) was used to characterize the biochemical properties of the protein and confirm expression of AAD-12 protein.

Levels of AAD-12 protein were determined in cotton event pDAB4468.18.07.1. Samples of cotton leaf tissue were isolated from the test plants and prepared for expression analysis. The AAD-12 protein was extracted from cotton plant tissues with a Tris-HCl solution containing the detergent Brij-56™ (Sigma-Aldrich, St. Louis, Mo.). The plant tissue was centrifuged; the aqueous supernatant was collected, diluted with appropriate buffer as necessary, and analyzed using an AAD-12 ELISA kit (Beacon Diagnostics, East Falmouth, Mass.) in a sandwich format. The kit was used following the manufacturer's suggested protocol.

Detection analysis was performed to investigate the expression stability and heritability both vertically (between generations) and horizontally (between lineages of the same generation) in cotton event pDAB4468.18.07.1. The AAD-12 protein expression of cotton event pDAB4468.18.07.1 was stable (not segregating) and consistent across all lineages.

AAD-12 protein expression levels as compared vertically (between generations) were determined for greenhouse grown cotton event pDAB4468.18.07.1 plants. Expression levels were consistent and stable across the $T_3$-$T_4$ generations with average expression levels of approximately 125-140 ng/cm$^2$ of isolated AAD-12 protein.

AAD-12 protein expression levels as compared horizontally (between lineages of the same generation) were determined for field grown cotton event pDAB4468.18.07.1 plants. Field expression level studies were performed on several cotton event pDAB4468.18.07.1 plants that comprised the $T_4$ generation. The average levels of protein expression were consistent and stable at approximately 50-150 ng/cm$^2$ of isolated AAD-12 protein.

Example 3: Cloning and Characterization of Genomic Flanking Border Regions of Cotton Event pDAB4468.18.07.1

Genomic flanking border regions which are adjacent to the cotton event pDAB4468.18.07.1 T-strand insert were isolated, cloned, and characterized. To characterize the border regions and describe the genomic insertion site, the genomic flanking regions of cotton event pDAB4468.18.07.1 were isolated, comprising 2,885 bp of the 5' genomic flanking border sequence (SEQ ID NO:1) and 902 bp of the 3' genomic flanking border sequence (SEQ ID NO:2). The cotton event pDAB4468.18.07.1 genomic flanking border sequences were BLASTed against the NCBI nucleotide database to confirm that these regions were of cotton origin. A BLAST of the 3' flanking border indicated that this sequence partially aligned to two different BAC Clones (*Gossypium hirsutum* MX146F18 and *Gossypium arboreturn* GM006001). Furthermore, the BLAST search indicated that cotton event pDAB4468.18.07.1 was located within the cotton genome on chromosome 26 of the D genome. Overall, the characterization of the genomic flanking border sequence of cotton event pDAB4468.18.07.1 indicated that a copy of the T-strand from pDAB4468 was present within the cotton genome.

Example 3.1: Confirmation of Cotton Genomic Sequences

Figure 2:
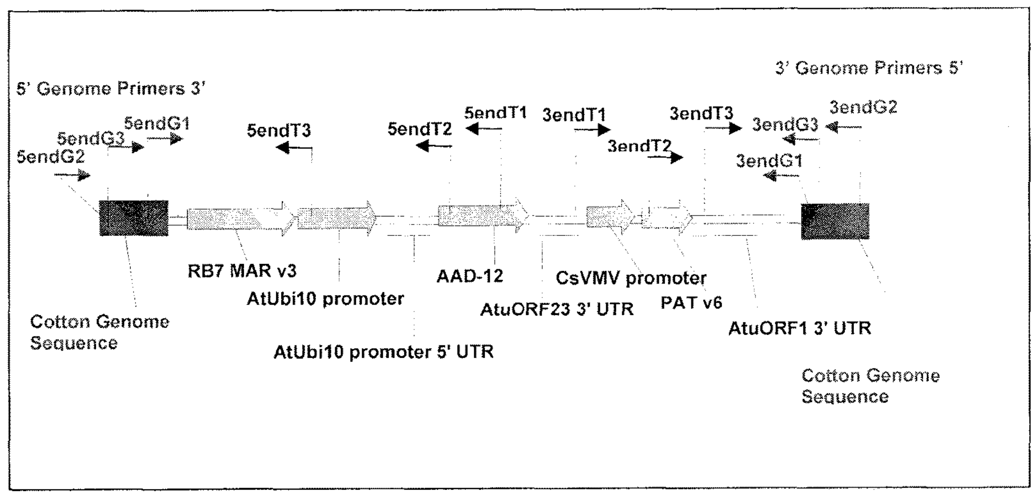
FIG. 2 depicts the primer locations for confirming the 5' and 3' border sequence of cotton event pDAB4468.18.07.1.

To confirm the sequence of the genomic insertion site of cotton event pDAB4468.18.07.1, a Polymerase Chain Reaction (PCR) was carried out with different pairs of primers (FIG. 2 and Table 2 and Table 3). Genomic DNA from cotton event pDAB4468.18.07.1 and other transgenic or non-transgenic cotton control lines were used as a template. The LA Taq PCR® kit was used for the reactions (TaKaRa, Japan).

TABLE 2

PCR primers and sequences used to analyze Cotton Event pDAB4468.18.07.1

| SEQ ID NO: | Abbreviation | Sequence Name | Sequence 5' to 3' | Purpose |
|---|---|---|---|---|
| SEQ ID NO: 4 | 3endG1 | 1807_3end_genome1 | TGTAGGTAAAAGATT AAACCATTGAGATG | confirmation of 3' border genomic DNA, used with 3endT1 and T3 |
| SEQ ID NO: 5 | 3endG2 | 1807_3end_genome2 | TGTGTGTTTTAGGTT GATTAGATTTATT | confirmation of 3' border genomic DNA, used with 3endT3 |
| SEQ ID NO: 6 | 3endG3 | 1807_3end_genome3 | TGAGAATAAGAGTTA TTTGAGAATAAGAGT | confirmation of 3' border genomic DNA, used with 3endT3 |
| SEQ ID NO: 7 | 5endG1 | 1807_5end_genome1 | GAAAGAGAAATGATG TATAAAGCAGGATT | confirmation of 5' border genomic DNA, used with 5endT1, T2, T3 |
| SEQ ID NO: 8 | 5endG2 | 1807_5end_genome2 | TGCTCACAGTGACTA ACATTACATGGAA | confirmation of 5' border genomic DNA, used with 5endT1, T2, T3 |
| SEQ ID NO: 9 | 5endG3 | 1807_5end_genome3 | CTATTTGAGAGAAGT AAGATGAAAGTCG | confirmation of 5' border genomic DNA, used with 5endT3 |
| SEQ ID NO: 10 | 5endG4 | 1807_5end_genome4 | ACAACATCGTGAATT ACATCAATAAGAAAG | confirmation of 5' border genomic DNA, used with 5endT1 and T3 |
| SEQ ID NO: 11 | 5endT1 | aad12_N1_primer | GTGTTGCCCAGGGA AGA | Transgene Primer 5' end |
| SEQ ID NO: 12 | 5endT2 | aad12_N2_primer | ATGTTGAAGCCAGGC TGC | Transgene Primer 5' end |
| SEQ ID NO: 13 | 5endT3 | ubi.for.primer | CACAGAAATTTACC TTGATCACGG | Transgene Primer 5' end |
| SEQ ID NO: 14 | 3endT1 | PAT.EXPRESSION CASSETTE.F_primer | CCAGAAGGTAATTA TCCAAGATGT | Transgene Primer 3' end |
| SEQ ID NO: 15 | 3endT2 | PAT.GOI.Primer | GACAGAGCCACAAA CACCACAAGA | Transgene Primer 3' end |
| SEQ ID NO: 16 | 3endT3 | Orf.F.Primer | AGATCGGCGGCAA TAGCTTCT | Transgene Primer 3' end |

TABLE 3

PCR conditions and reaction mixture for amplification of border regions and event-specific sequences in cotton event pDAB4468.18.07.1.

| Reagent | Amount (μL) of Reagent | PCR Cycling Parameters | |
|---|---|---|---|
| LA Buffer + $MgCl_2$ | 5.0 | | |
| dNTP's at 2.5 mM | 8.0 | 95° C. 5 min | |
| Primer Genome (10 μM) | 1.0 | 98° C. 10 s | 35 X |
| Primer Transgene (10 μM) | 1.0 | 60° C. 30 s | 35 X |
| 10% PVP | 0.5 | 72° C. 4 min | 35 X |
| La Taq Polymerase | 0.5 | 72° C. 10 min | |
| $H_2O$ | 31.5 | 4° C. hold | |
| DNA (20 ng/μL) | 2.5 | | |
| Total Volume | 50.0 | | |

The 5' genomic flanking border sequences were PCR amplified and sequenced. These reactions used aad-12 expression cassette specific primers, (for example, 5endT1, 5endT2 and 5endT3) and primers designed according to the cloned 5' end border sequence obtained from the cotton genome (for example, 5endG1 and 5endG2 and 5endG3) to amplifying a genomic DNA segment that spans the aad-12 gene and 5' end genomic flanking border sequence. Similarly, for confirmation of the cloned 3' genomic flanking border sequence, pat expression cassette specific primers, (for example, 3endT1, 3endT2 and 3endT3) and primers designed according to the cloned 3' end border sequence (for example, 3endG1, 3endG2 and 3endG3) were used to amplify a genomic DNA segment that spans the pat gene and the 3' end genomic flanking border sequence. DNA fragments of expected size were amplified from the genomic DNA of cotton event pDAB4468.18.07.1 with each primer pair (one primer located on the flanking border of cotton event pDAB4468.18.07.1 and one transgene specific primer). The control samples (other transgenic cotton lines or non-transgenic control line, Coker 310) did not produce PCR amplicons using these primers. The PCR amplicons were subcloned into plasmids and sequenced. This data was used to determine the 5' and 3' genomic flanking border sequences located adjacent to the T-strand insert of cotton event pDAB4468.18.07.1.

Example 4: Cotton Event pDAB4468.18.07.1 Characterization by Southern Blot

Southern blot analysis was used to establish the integration pattern of cotton event pDAB4468.18.07.1. These experiments generated data which demonstrated the integration and integrity of the aad-12, and pat transgenes within the cotton genome. Cotton event pDAB4468.18.07.1 was characterized as a full length, simple integration event containing a single copy of the aad-12 and pat expression cassette from plasmid pDAB4468.

Southern blot data suggested that a T-strand fragment inserted into the genome of cotton event pDAB4468. Detailed Southern blot analysis was conducted using a probe specific to the aad-12 and pat genes, contained in the T-strand integration region of pDAB4468, and descriptive restriction enzymes that have cleavage sites located within the plasmid and produce hybridizing fragments internal to the plasmid or fragments that span the junction of the plasmid and cotton genomic DNA (border fragments). The molecular weights indicated from the Southern hybridization for the combination of the restriction enzymes and the probes were unique for the event, and established its identification pattern. These analyses also showed that the pDAB4468 T-strand fragment had been inserted into the cotton genomic DNA without rearrangements of the aad-12 or pat expression cassettes.

Example 4.1: Cotton Leaf Sample Collection and Genomic DNA Isolation

Genomic DNA was extracted from leaf tissue harvested from individual cotton plants containing cotton event pDAB4468.18.07.1. In addition, gDNA was isolated from a conventional cotton plant, Coker 310, which contains the genetic background that is representative of the cotton line used for transformation and does not contain the aad-12 and pat genes. Individual genomic DNA was extracted from lyophilized leaf tissue following the standard manufacturer's protocol using the Qiagen Dneasy Mini Prep DNA Extraction Kit® (Qiagen, CA). Following extraction, the DNA was quantified spectrofluorometrically using Pico Green® reagent (Invitrogen, Carlsbad, Calif.) and utilizing the Nanodrop® instrumentation (Invitrogen). The DNA was then visualized on an agarose gel to confirm values from the Pico Green® analysis and to determine the DNA quality.

Example 4.2: gDNA Digestion and Separation

For Southern blot characterization of cotton event pDAB4468.18.07.1, ten micrograms (10 μg) of genomic DNA was digested. Genomic DNA from cotton event pDAB4468.18.07.1 and the non-transgenic cotton line, Coker 310, was digested by adding approximately 10 units of selected restriction enzyme per μg of DNA and the corresponding reaction buffer to each DNA sample. Each sample was incubated at approximately 37° C. overnight. The restriction enzymes NsiI, NcoI, SbfII, SwaI, and NdeI were used individually for the digestion reactions (New England Biolabs, Ipswich, Mass.). In addition, a positive hybridization control sample was prepared by combining plasmid DNA, pDAB4468, with genomic DNA from the non-transgenic cotton variety, Coker310. The plasmid DNA/genomic DNA cocktail was digested using the same procedures and restriction enzyme as the test samples. After the digestions were incubated overnight, NaCl was added to a final concentration of 0.1 M to stop the restriction enzyme digestion reaction. The digested DNA samples were precipitated with isopropanol. The precipitated DNA pellet was resuspended in 15 μl of 3× loading buffer (0.01% bromophenol blue, 10.0 mM EDTA, 5.0% glycerol, 1.0 mM Tris pH 7.5). The DNA samples and molecular size marker were then electrophoresed through 0.85% agarose gels with 0.4×TAE buffer (Fisher Scientific, Pittsburgh, Pa.) at 45 volts for approximately 18-22 hours to achieve fragment separation. The gels were stained with ethidium bromide (Invitrogen, Carlsbad, Calif.) and the DNA was visualized under ultraviolet (UV) light.

Example 4.3: Southern Transfer and Membrane Treatment

Southern blot analysis was performed essentially as described by Memelink, J., Swords, K., Harry J., Hoge, C., (1994) Southern, Northern, and Western Blot Analysis. *Plant Mol. Biol. Manual F*1:1-23. Briefly, following electrophoretic separation and visualization of the DNA fragments, the gels were denatured with 1× Denaturation Solution (1.5 M NaOH, 20 mM EDTA) for exactly 20 minutes, and then washed with 1× Neutralization Solution (1.5 M $NaPO_4$, pH 7.8) for at least 20 minutes. Southern transfer was performed overnight onto nylon membranes using a wicking system with 1× Transfer solution (0.25 M Sodium Pyrophosphate, pH 10). After transfer the DNA was bound to the membrane by heating at 65° C. for 1 hour or by UV crosslinking followed by briefly washing membrane with 1× Transfer solution. This process produced Southern blot membranes ready for hybridization.

Example 4.4: DNA Probe Labeling and Hybridization

The DNA fragments bound to the nylon membrane were detected using a $P^{32}$ radio-labeled probe. Probes were generated by a PCR-based method using primers specific to gene elements, and following standard manufacturer's procedure with the HotStar® Taq polymerase (Qiagen, CA). 50 ng of probe DNA specific for each gene element and 25 ng 1 Kb plus ladder (Invitrogen, Carlsbad, Calif.) were labeled with $P^{32}$ using Ready to Go Labeling Beads® (Amersham, Piscataway, N.J.) following the manufacturer's instructions. Probes were purified using the Nucleotide G-50® spin column from Amersham following the manufacturer's protocol.

Before addition of the $P^{32}$ radiolabeled probe, the nylon membrane blots containing fixed DNA were blocked with Blocking buffer: (2% SDS, 0.5% BSA, 1 mM EDTA, 1 mM orthophenanthroline) for at least 2 hours at room temperature on a shaker, and were then pre-hybridized with 10 ml of Perfect HYB Plus Buffer® (Sigma-Aldrich, St. Louis, Mo.) at 65° C. for at least 1 hour in a hybridization oven. Purified labeled probes were denatured in a boiling water bath for 5 minutes and placed on ice for 5 minutes and then added to the blocked and pre-hybridized membranes and placed overnight at 65° C. in a hybridization oven.

After probe hybridization, the probe solution was discarded into radioactive waste. The membrane blots were washed twice in their original hybridization tube with 1× Ribowash™: (200 mM Sodium Phosphate, 50 mM Sodium Pyrophosphate, 10 mM EDTA, 2% SDS, pH to 7.8) wash buffer for 15 minutes each wash in a 65° C. hybridization oven. Each wash was discarded into the radioactive liquid waste following standard operating procedures. Membranes were removed from the tube and placed in a clean rinsing tray and washed once more in a shaker incubator at 65° C. for an additional 15 minutes. Membranes were wrapped in plastic wrap, placed in a film cassette and exposed to a phoshor imager screen for 1 to 3 days. Images were obtained using the BioRad Personal FX Phosphor Imager® following equipment and software guidelines.

The probes used for the hybridization are described in Table 4. The 1 Kb Plus DNA Ladder (Invitrogen, Carlsbad, Calif.) was used to determine hybridizing fragment size on the Southern blots.

TABLE 4

Length of probes used in Southern analysis of cotton event pDAB4468.18.07.1

| Probe Name | Genetic Element | Length (bp) |
|---|---|---|
| aad-12 | aad-12 | 671 |
| Pat | pat | 525 |
| specR | Spectinomycin resistance gene | 750 |
| OriRep | Ori Rep | 852 |
| trfA | Replication initiation protein trfA | 1119 |

Example 4.5: Southern Blot Results

Expected and observed fragment sizes with a particular digest and probe, based on the known restriction enzyme sites of the aad-12 and pat gene expression cassette, are given in Table 5. Expected fragment sizes are based on the plasmid map of pDAB4468 and observed fragment sizes are approximate results from these analyses and are based on the correspondence of the band with the indicated sizes of the 1 Kb Plus DNA Ladder.

Two types of fragments were identified from these digests and hybridizations: internal fragments where known enzyme sites flank the probe region and are completely contained within the insertion region of the aad-12 expression cassette, and border fragments where a known enzyme site is located at one end of the probe region and a second site is expected in the cotton genome. Border fragment sizes vary by event because, in most cases, DNA fragment integration sites are unique for each event. The border fragments provide a means to locate a restriction enzyme site relative to the integrated DNA and to evaluate the number of DNA insertions. Southern blot analyses completed on multiple generations of cotton lines containing cotton event pDAB4468.18.07.1 produced data which suggested that a low copy, intact aad-12 expression cassette from plasmid pDAB4468 was inserted into the cotton genome thereby resulting in cotton event pDAB4468.18.07.1.

The restriction enzymes NsiI and SwaI bind and cleave unique restriction sites within plasmid pDAB4468. Subsequently, these enzymes were selected to characterize the aad-12 gene insert in cotton event pDAB4468.18.07.1. Border fragments of greater than 6.3 Kb or greater than 4.3 Kb were predicted to hybridize with the probe following digests, respectively (Table 5). Single aad-12 hybridization bands of approximately 8.0 Kb and approximately 5.0 Kb were observed when NsiI, and SwaI were used, respectively. In addition, restriction enzyme NcoI was selected to characterize the aad-12 gene insert. The plasmid used to produce cotton event pDAB4468.18.07.1, pDAB4468, contained a unique NcoI restriction site in the expression cassette of plasmid pDAB4468, and two additional sites in the "backbone" area of plasmid pDAB4468. A border fragment of greater than 3.7 Kb was predicted to hybridize with the probe following digests (Table 5). A single aad-12 hybridization band of approximately 10.5 Kb was observed. The hybridization of the probe to bands of this size suggests the presence of a single site of insertion for the aad-12 gene in the cotton genome of cotton event pDAB4468.18.07.1. Three combinations of restriction enzymes, Nde, NsiI+NcoI and NsiI+SbfI, were selected to release a fragment which contains various regions of the aad-12 expression cassette and the pat expression cassette (Table 5). The NdeI restriction enzyme includes the aad-12 expression cassette elements from the Ubi10 Promoter to the AtuORF23 UTR terminator. A predicted fragment of 3.5 Kb was observed on blots probed with the aad-12 probe following the NdeI digest. The double digestion with NsiI and NcoI includes the aad-12 and pat expression cassette elements. A predicted fragment of 3.5 Kb was observed on blots probed with the aad-12 probe following the double enzyme digestion. (Table 5). The double digestion with NsiI and SbfI contains both aad-12 and pat expression cassette elements. A predicted fragment of 4.8 Kb was observed on blots probed with aad-12 following the double enzyme digestion. (Table 5).

In addition, hybridization bands were observed on blots which were probed with a pat probe and digested with the restriction enzyme digestions described above (NsiI, NcoI, SwaI, NdeI, NsiI+NcoI and NsiI+SbfI). The resulting blots produced fragments which indicate that the pat expression cassette was present in cotton event pDAB4468.18.07.1. Table 5 lists the expected fragment sizes which are based on the plasmid map of pDAB4468, in addition to the observed fragment sizes which resulted from the Southern blots probed with pat. These results obtained for cotton event pDAB4468.18.07.1 indicate that an intact aad-12 expression cassette and pat expression cassette from plasmid pDAB4468 was inserted into the cotton genome of the cotton event pDAB4468.18.07.1.

Example 4.6: Absence of Backbone Sequences

Southern blot analysis was also conducted to verify the absence of the spectinomycin resistance gene (specR), Ori Rep element and replication initiation protein trfA (trf A element) in cotton event pDAB4468.18.07.1. Following NsiI digestion and hybridization with a specR specific probe, one expected size band of approximately 12 Kb was observed in the positive control sample (pDAB4468 plus Coker 310) but absent from samples of the negative control and cotton event pDAB4468.18.07.1. Similarly, one expected size band of approximately 7.25 Kb was detected in the positive control sample (pDAB4468 plus Coker 310) but absent from the samples of the negative control and cotton event pDAB4468.18.07.1 after NcoI digestion and hybridization with a mixture of OriRep specific probe and trfA specific probe. This data indicates the absence of the spectinomycin resistance gene, Ori Rep element and replication initiation protein trfA in cotton event pDAB4468.18.07.1.

TABLE 5

Predicted and Observed Hybridizing Fragments in Southern Blot Analysis.

| DNA Probe | Restriction Enzymes | Samples | Expected Fragment Sizes (bp)[1] | Observed Fragment Size (bp)[2] |
|---|---|---|---|---|
| aad-12 | NsiI | pDAB4468 | >11.0 Kb | >11.0 Kb |
| | | Coker 310 | None | None |
| | | Cotton Event pDAB4468.18.07.1 | >6.3 Kb | ~8.0 Kb |
| | NcoI | pDAB4468 | 7.4 Kb | ~7.0 Kb |
| | | Coker 310 | None | None |
| | | Cotton Event pDAB4468.18.07.1 | >3.7 Kb | 10.5 Kb |
| | SwaI | pDAB4468 | >11.0 Kb | >11.0 Kb |
| | | Coker 310 | None | None |
| | | Cotton Event pDAB4468.18.07.1 | >4.3 Kb | 5.0 Kb |
| | NdeI | pDAB4468 | 3.5 Kb | 3.5 Kb |
| | | Coker 310 | None | None |
| | | Cotton Event pDAB4468.18.07.1 | 3.5 Kb | 3.5 Kb |
| | NsiI + NcoI | pDAB4468 | 3.5 Kb | 3.5 Kb |
| | | Coker 310 | None | None |
| | | Cotton Event pDAB4468.18.07.1 | 3.5 Kb | 3.5 Kb |
| | NsiI + SbfI | pDAB4468 | 4.8 Kb | 4.8 Kb |
| | | Coker 310 | None | None |
| | | Cotton Event pDAB4468.18.07.1 | 4.8 Kb | 4.8 Kb |
| pat | NsiI | pDAB4468 | >11.0 Kb | >11.0 Kb |
| | | Coker 310 | None | None |
| | | Cotton Event pDAB4468.18.07.1 | >6.3 Kb | ~8.0 Kb |
| | NcoI | pDAB4468 | 7.4 Kb | ~7.3 Kb |
| | | Coker 310 | None | None |
| | | Cotton Event pDAB4468.18.07.1 | >3.7 Kb | 10.5 Kb |

TABLE 5-continued

Predicted and Observed Hybridizing Fragments in Southern Blot Analysis.

| DNA Probe | Restriction Enzymes | Samples | Expected Fragment Sizes (bp)[1] | Observed Fragment Size (bp)[2] |
|---|---|---|---|---|
| | SwaI | pDAB4468 | >11.0 Kb | >11.0 Kb |
| | | Coker 310 | None | None |
| | | Cotton Event pDAB4468.18.07.1 | >2.25 Kb | 5.0 Kb |
| | NdeI | pDAB4468 | 5.25 Kb | 5.25 Kb |
| | | Coker 310 | None | None |
| | | Cotton Event pDAB4468.18.07.1 | >2.4 Kb | ~12 Kb |
| | NsiI + NcoI | pDAB4468 | 3.5 Kb | 3.5 Kb |
| | | Coker 310 | None | None |
| | | Cotton Event pDAB4468.18.07.1 | 3.5 Kb | 3.5 Kb |
| | NsiI + SbfI | pDAB4468 | 4.8 Kb | 4.8 Kb |
| | | Coker 310 | None | None |
| | | Cotton Event pDAB4468.18.07.1 | 4.8 Kb | 4.8 Kb |
| SpecR | NsiI | pDAB4468 | 12 Kb | >12 Kb |
| | | Coker 310 | None | None |
| | | Cotton Event pDAB4468.18.07.1 | None | None |
| OriRep and trfA | NcoI | pDAB4468 | 7.25 Kb | 7.25 Kb |
| | | Coker 310 | None | None |
| | | Cotton Event pDAB4468.18.07.1 | None | None |

[1]Expected fragment sizes are based on the plasmid map of pDAB4468.
[2]Observed fragment sizes are considered approximately from these analyses and are based on the indicated sizes of the $P^{32}$-labeled DNA Molecular Weight fragments.

Example 5: Tolerance to 2,4-D in Field Trials

The tolerance of cotton event pDAB4468.18.07.1 to postemergence applications of the phenoxyacetic acid herbicide, 2,4-D, was studied in field trials during the 2010 growing season. Herbicide tolerance was assessed following a single postemergence application of 2,4-D applied to 2-4 leaf cotton event pDAB4468.18.07.1. The application of 2,4-D on cotton plants at this stage of development represents a herbicide application timing typically utilized to achieve satisfactory weed control by cotton growers.

2,4-D tolerance was measured by assessing cotton plants for injury at 0-1 day after application (DAA), 7-8 DAA, 12-16 DAA, and 24-32 DAA. Measurements for the 0-1 day time increment were taken from 6-24 hours after the application. Injury was assessed by assigning a percent visual injury rating using a linear percentage scale (1-100%) where 0% represents no visible herbicide injury and 100% represents plant death. The ratings were a composite score for any herbicide symptomology including epinasty, chlorosis, leaf necrosis and plant death. Herbicide symptomology present at 0-1 DAA was primarily epinasty and symptoms at later evaluations were primarily chlorosis and necrosis.

Field trials were conducted at eleven locations across the United States in typical cotton producing areas of Alabama, Arkansas, California, Georgia, Louisiana, Mississippi, North Carolina, South Carolina, and Tennessee. Trials were designed with four replications per treatment. Each replication was separated by a bare-soil alley 10-15 feet wide. Plot size for individual treatments was 2 rows by 20 feet long with rows typically spaced 36-40 inches apart. Experimental treatments consisted of cotton event pDAB4468.18.07.1 sprayed with 2,4-D amine (Weedar 64™, NuFarm, Burr Ridge, Ill.) at either 0, 1120, 2240, or 4480 grams acid equivalent per hectare (g ae/ha) applied in 15 gallons per acre of final spray solution. A non-transformed cotton comparator treatment was not included in these experiments since treatment with 2,4-D at rates much lower than the lowest rate tested (1120 g ae/ha) are known to result in plant death.

Table 6 presents the treatment means for visual injury resulting from postemergence application of 2,4-D. With the exception of transient epinasty 0-1 DAA, no agronomically-significant herbicide injury was noted in these experiments. Treatment with 2,4-D at 4480 g ae/ha (which represents a rate anticipated to be >4× that required for broad spectrum weed control) resulted in little crop injury beyond the 7-8 DAA evaluation interval and demonstrates the robust tolerance of cotton event pDAB4468.18.07.1 to 2,4-D.

TABLE 6

Percent visual injury for cotton event pDAB4468.18.07.1 following postemergence application of 2,4-D.

| 2,4-D Rate (g ae/ha) | 0-1 DAA | 7-8 DAA | 12-16 DAA | 24-32 DAA |
|---|---|---|---|---|
| 0 | 0.0 | 0.0 | 0.0 | 0.0 |
| 1120 | 5.0 | 2.3 | 1.1 | 0.0 |
| 2240 | 11.7 | 4.9 | 2.7 | 0.4 |
| 4480 | 21.0 | 15.1 | 8.0 | 2.2 |

Example 6: Tolerance to Glufosinate in Field Trials

The tolerance of cotton event pDAB4468.18.07.1 to postemergence applications of glufosinate was studied in field trials during the 2010 growing season. Herbicide tolerance was assessed following a single postemergence application of glufosinate applied to 6-8 leaf cotton event pDAB4468.18.07.1, which represents a herbicide application timing typically utilized with glufosinate to achieve satisfactory weed control.

Glufosinate tolerance was measured by assessing cotton plants for injury at 2-4 days after application (DAA), 7-9 DAA, 13-19 DAA and 22-29 DAA. Injury was assessed by assigning a percent visual injury rating using a linear percentage scale (1-100) where 0% represents no visible herbicide injury and 100% represents plant death. The ratings were a composite score for any herbicide symptomology including chlorosis, leaf necrosis, stunting and plant death. Herbicide symptomology (where present) was primarily chlorosis and necrosis.

Field trials were conducted at eleven locations across the United States in typical cotton producing areas of Alabama, Arkansas, California, Georgia, Louisiana, Mississippi, North Carolina, South Carolina, and Tennessee. Trials were designed with four replications per treatment. Each replication was separated by a bare-soil alley 10-15 feet wide. Plot size for individual treatments was 2 rows by 20 feet long with rows typically spaced 36-40 inches apart. Experimental treatments consisted of cotton event pDAB4468.18.07.1 sprayed with glufosinate ammonium (Ignite 280 SL™, Bayer, Research Triangle, N.C.) at either 0, 542, 1084, or 2168 grams acid equivalent per hectare (g ae/ha) applied in 15 gallons per acre of final spray solution. A non-transformed cotton comparator treatment was not included in these experiments since treatment with glufosinate at rates much lower than the lowest rate tested (542 g ae/ha) would be expected to result in plant death.

Table 7 presents the treatment means for visual injury resulting from postemergence application of glufosinate. With the exception of transient chlorosis in the plots treated with 2168 g ae/ha (>4× the typical use rate) at 2-4 & 7-9 DAA, no agronomically-significant herbicide injury was noted in these experiments. Treatment with glufosinate 2168 g ae/ha (which represents a rate anticipated to be >4× that required for broad spectrum weed control) resulted in little crop injury beyond the 7-9 DAA evaluation interval and demonstrates the robust tolerance of cotton event pDAB4468.18.07.1.

TABLE 7

Percent visual injury for cotton event pDADB4468.18.07.1 following postemergence application of glufosinate.

| Glufosinate Rate (g ae/ha) | 2-4 DAA | 7-9 DAA | 13-19 DAA | 22-29 DAA |
|---|---|---|---|---|
| 0 | 0.0 | 0.0 | 0.1 | 0.0 |
| 542 | 3.1 | 2.3 | 0.1 | 0.1 |
| 1084 | 7.6 | 4.8 | 0.1 | 0.0 |
| 2168 | 14.8 | 10.8 | 2.2 | 0.3 |

Example 7: Tolerance to Triclopyr and Fluroxypyr in Greenhouse Trials

The tolerance of cotton event pDAB4468.18.07.1 to postemergence applications of the pyridyloxyacetic acid herbicides, triclopyr and fluroxypyr, was studied in greenhouse trials. Herbicide tolerance was assessed following a single postemergence application of triclopyr or fluroxypyr.

Seeds from cotton event pDAB4468.18.07.1 were heat treated in a water bath at 82.5° C. for 1 minute and then planted in metro mix 360 media and grown in a greenhouse. The temperatures in the greenhouse averaged 27° C. and the photoperiod was set at 16 hours of light and eight hours of dark, with maximum light intensity. Plants were allowed to grow until the 3 leaf stage of development and a non-randomized study was conducted with three replications and three treatments for each herbicide. Plants were sprayed in a track sprayer calibrated to deliver 187 L/ha of the commercial formulations of triclopyr (Garton 4™, Dow AgroSciences, Indianapolis, Ind.) and fluroxypyr (Starane™, Dow AgroSciences, Indianapolis, Ind.). A non-transformed Coker 310 variety of cotton was used as a negative control. Visual injury assessment was taken 3 DAA (days after application) and 11 DAA comparing each rate of herbicide. Injury was assessed visually as percentage of epinastic cotton-plant foliage using a linear percentage scale (1-100%) where 0% represents no visible herbicide injury and 100% represents plant death.

Cotton event pDAB4468.18.07.1 provides tolerance to levels of fluroxypyr up to 280 g ae/ha by 3 DAA (Table 8). In addition, cotton event pDAB4468.18.07.1 provides tolerance to triclopyr (Table 8). At 3 DAA the cotton event pDAB4468.18.07.1 plants demonstrated moderate levels of tolerance to triclopyr, but by 11 DAA the plants had recovered from the initial epinastic response and provided robust tolerance compared to the non-transformed control. The resulting study demonstrates that cotton event pDAB4468.18.07.1 provides tolerance to the pyridyloxyacetic acid herbicides, triclopyr and fluroxypyr.

TABLE 8

Percent visual injury following postemergence application of the herbicides triclopyr and fluroxypyr.

| | | % Injury | | | |
|---|---|---|---|---|---|
| | | 3 DAA | | 11 DAA | |
| Herbicide | Rate (g ae/ha) | Cotton event pDAB4468.18.07.1 | Coker Control | Cotton event pDAB4468.18.07.1 | Coker Control |
| Triclopyr | 140 | 11.8 b | 33.8 a | 3.0 a | 36.3 b |
| Triclopyr | 280 | 17.0 a | 33.8 a | 6.3 a | 40.0 ab |
| Triclopyr | 560 | 19.3 a | 36.3 a | 3.5 a | 48.8 a |
| Fluroxypyr | 70 | 1.8 c | 11.3 c | 4.8 a | 43.8 ab |
| Fluroxypyr | 140 | 1.0 c | 27.3 b | 4.3 a | 36.3 b |
| Fluroxypyr | 280 | 5.5 c | 33.3 a | 8.0 a | 43.8 ab |
| Least Significant Difference (p = .05) | | 3.98 | 4.78 | 4.07 | 6.95 |
| Standard Deviation | | 2.68 | 3.22 | 2.74 | 4.68 |

Means followed by same letter do not significantly differ (P = .05, Student -Newman-Keuls).

Example 8: Agronomic Characterization of Cotton Event pDAB4468.18.07.1

The agronomic characteristics of cotton event pDAB4468.18.07.1 were quantified in field trials conducted across geographically different locations throughout the cotton belt in 2010. These studies compared the agronomic performance of cotton event pDAB4468.18.07.1 (with and without applications of the herbicides 2,4-D and glufosinate) to the non-transgenic near-isoline control, Coker 310. No agronomically meaningful unintended differences were observed between cotton event pDAB4468.18.07.1 and the Coker 310 control plants. The results of these field trials demonstrated that cotton event pDAB4468.18.07.1 was agronomically equivalent to the Coker 310 control plants and that the presence of the T-strand insert from pDAB4468 did not alter the expected agronomic performance of cotton event pDAB4468.18.07.1. Additionally, the agronomic performance of cotton event pDAB4468.18.07.1 was not altered as a result of the application of the herbicides, 2,4-D and glufosinate, as compared to the cotton event pDAB4468.18.07.1 plants which were not sprayed with the herbicide treatments.

Evaluations of agronomic characteristics were made for seedling vigor, % plant emergence, flower initiation, nodes after white flower (NAWF), and yield determination using the criteria indicated in Table 9. Harvested fiber was sent to the Fiber and Biopolymer Research Institute in Lubbock, Tex. for fiber evaluation using the High Volume Instrument (HVI).

TABLE 9

Agronomic characteristics evaluated in yield trials.

| Parameter | Timing | Description | Scale |
|---|---|---|---|
| % Plant emergence | 7 days after planting (DAP) | Cotyledons have assumed an erect posture and are completely unrolled | Total number of plants that are in rows 2 and 3 of the four row plots |
| Seedling vigor ratings | 7 and 28 DAP | Determined by assessing the health of the plot | 1-5 scale (1 = healthy and growing well; 5 = living but off color, not growing, and may not survive) |
| Days till first white flower | ~60 DAP | 50% of the plants in the plot have produced at least one white flower on a sympodial branch | Date |
| Nodes after white flower (NAWF) | 2 weeks after flower initiation | Recorded the number of mainstem nodes between the uppermost sympodial branch with a first position white flower and the plant terminal on 5 randomly selected plants per plot. The terminal node is considered to be the uppermost with a leaf >25 mm wide. Continued the evaluation weekly until the trial average reached NAWF = 5 or cutoff. | NAWF = 5 or cutoff the experiment |
| Cotton yield (lbs) | Upon harvest | Refers to the weight of pounds of cotton per acre | Pounds of cotton per acre |
| Lint yield (lbs) | Upon harvest | Refers to the measure of the quantity of fiber produced on a given unit of land. Presented in pounds of lint per acre | Pounds of lint per acre |

Seeds of cotton event pDAB4468.18.07.1 and seeds of the near-isoline control line, Coker 310, were planted at a rate of 80 seeds per 20 ft row with a row spacing of 34-38 inches (86.36 cm-96.52 cm). This planting design was replicated four times at each site. Each site was arranged in a complete randomized block design (CRBD) consisting of 3 unsprayed blocks and 4 sprayed blocks for each replication. Plants were sprayed with the herbicides 2,4-D and glufosinate using standard field application rates and methods as described above. The center two rows (rows 2 and 3) were used to measure the agronomic characteristics and evaluate the plants. The measured agronomic characteristics were equivalent for cotton event pDAB4468.18.07.1 as compared to the Coker 310 near-isoline control plants for all of the agronomic characteristics measured and statistically analyzed. One exception was identified for the "% plant emergence" results within the herbicide sprayed plots of cotton event pDAB4468.18.07.1. However, the "% plant emergence" data points were taken before the application of any herbicide and the variability in this measurement is attributed to environmental factors. No agronomically meaningful unintended differences were observed between cotton event pDAB4468.18.07.1 and the Coker 310 control plants. These field trials demonstrated that cotton event pDAB4468.18.07.1 was agronomically equivalent to the Coker 310 control plants and that the presence of the T-strand insert from pDAB4468 did not alter the expected agronomic performance of cotton event pDAB4468.18.07.1. Additionally, the agronomic performance of cotton event pDAB4468.18.07.1 was not altered as a result of the application of the herbicides, 2,4-D and glufosinate, as compared to the cotton event pDAB4468.18.07.1 plants which were not sprayed with the herbicide treatments.

TABLE 10

Statistical data for treated (sprayed with herbicide) and non-treated (unsprayed with herbicide) events as compared to an near-isoline control cotton plant.

| Parameter | Coker 310 (near-isoline control) | Cotton event pDAB4468.18.07.1 unsprayed (P-value) | Cotton event pDAB4468.18.07.1 sprayed with herbicide (P-value) | Overall treatment effect (PR >F) |
|---|---|---|---|---|
| Plant emergence (7DAP) | 70.3 | 65.8 (0.29) | 64.2 (0.045) | 0.553 |
| Vigor ratings | 1.96 | 2.3 (0.1362) | 2.14 (0.22) | 0.303 |
| Days till first white flower (~60 DAP) | 56.9 | 57.79 (0.3883) | 57.79 (0.364) | 0.645 |
| NAWF (no.) | 4.92 | 4.95 (0.8919) | 5.15 (0.2539) | 0.4348 |
| Cotton yield (lbs) | 1825.43 | 2173.15 (0.4726) | 1678.6 (0.6544) | 0.8986 |
| Lint yield (lbs) | 831.63 | 782.81 (0.2359) | 792.43 (0.2887) | 0.5627 |

Example 9: Expected Sequence of Cotton Event pDAB4468.18.07.1

SEQ ID NO:17 provides the expected sequence of cotton event pDAB4468.18.07.1. This sequence contains the 5' genomic flanking sequence, the expected T-strand insert of pDAB4468 and the 3' genomic flanking sequence. With respect to SEQ ID NO:17, residues 1-2,885 are 5' genomic flanking sequence, residues 2,886-9,253 are residues of the pDAB4468 T-strand insert, and residues 9,254-10,156 are 3' flanking sequence. The junction sequence or transition with respect to the 5' end of the insert thus occurs at residues 2,885/2,886 of SEQ ID NO:17. The junction sequence or transition with respect to the 3' end of the insert thus occurs at residues 9,253/9,254 of SEQ ID NO:17.

It should be noted that SEQ ID NO:17 is the expected representation of cotton event pDAB4468.18.07.1 and was assembled from an alignment of SEQ ID NO:1, SEQ ID NO:2, and the T-strand of pDAB4468, SEQ ID NO:3. The actual sequence of the T-strand insert of cotton event pDAB4468.18.07.1 may slightly deviate from SEQ ID NO:17. During the transformation process of introducing an T-stand insert into the genome of plant cells, it is not uncommon for some deletions or other alterations of the insert to occur. Moreover, errors in PCR amplification can occur which might result in minor sequencing errors. For example, flanking sequences listed herein were determined by generating amplicons from cotton genomic DNAs, and then cloning and sequencing the amplicons. It is not unusual to find slight differences and minor discrepancies in sequences generated and determined in this manner, given the many rounds of amplification that are necessary to generate enough amplicon for sequencing from genomic DNAs. One skilled in the art should recognize and be put on notice that any adjustments needed due to these types of common sequencing errors or discrepancies are within the scope of embodiments of the subject invention. Thus, the relevant segment of the plasmid sequence provided herein might comprise some minor variations. Thus, a plant comprising a polynucleotide having some range of identity with the subject insert sequence is within the scope of embodiments of the subject invention. Specifically, a polynucleotide sequence having at least 90%, 91%, 92%, 93%, 94%, 95%, 96%, 97%, 98%, 99%, or 100% sequence identity to the sequence of SEQ ID NO:17 is within the scope of embodiments of the subject invention. The sequence of the flanking sequences plus insert sequence can be confirmed with reference to the deposited seed. Thus, some differences between SEQ ID NO:17 and the actual T-strand insert of cotton event pDAB4468.18.07.1 may be identified and are within the scope of embodiments of the present invention.

What is claimed is:

1. A nucleic acid molecule comprising SEQ ID NO:17.

2. A cotton seed comprising in its genome event pDAB4468.18.07.1, wherein the event comprises the polynucleotide of SEQ ID NO:17.

3. A method of breeding a cotton plant comprising:

crossing the cotton plant of claim 2 with a second cotton plant to produce a third cotton plant; and assaying the third cotton plant for the presence of one or more polynucleotides selected from the group consisting of nucleotides 2867-2906 of SEQ ID NO:1; nucleotides 2837-2936 of SEQ ID NO:1; nucleotides 2787-2986 of SEQ ID NO:1; nucleotides 2737-3036 of SEQ ID NO:1; nucleotides 128-167 of SEQ ID NO:2; nucleotides 98-197 of SEQ ID NO:2; nucleotides 48-247 of SEQ ID NO:2; nucleotides 1-297 of SEQ ID NO:2, and complete complements thereof.

4. The cotton seed of claim 2, the cotton seed comprising in its genome event pDAB4468.18.07.1, wherein a cotton seed representative of the seed comprising the event in its genome has been deposited with the American Type Culture Collection under Accession No. PTA-12456.

5. A cotton plant comprising in its genome event pDAB4468.18.07.1, wherein the event comprises the polynucleotide of SEQ ID NO:17.

6. A part of the cotton plant of claim 5, wherein the part is selected from the group consisting of pollen, ovule, flowers, bolls, shoots, roots, and leaves, wherein the part comprises the polynucleotide of SEQ ID NO:17.

7. A cotton meal or cotton oil produced from the cotton plant of claim 5, wherein the cotton meal or cotton oil comprises the polynucleotide of SEQ ID NO:17.

8. The cotton plant of claim 5, wherein the plant comprises in its genome event pDAB4468.18.07.1, representative seed of the plant having been deposited with the American Type Culture Collection under Accession No. PTA-12456.

9. A method of controlling weeds in a cotton crop comprising a plurality of the cotton plants of claim 5, the method comprising applying phenoxyacetic acid herbicide to the cotton crop.

10. The method of claim 9, wherein the phenoxyacetic acid herbicide is 2,4-D.

11. The method of claim 9, wherein the phenoxyacetic acid herbicide is MCPA.

12. A method of controlling weeds in a cotton crop comprising a plurality of the cotton plants of claim 5, the method comprising applying pyridyloxyacetic acid herbicide to the cotton crop.

13. The method of claim 12, wherein the pyridyloxyacetic acid herbicide is triclopyr.

14. The method of claim 12, wherein the pyridyloxyacetic acid herbicide is fluroxypyr.

15. A method of controlling weeds in a cotton crop comprising a plurality of the cotton plants of claim 5, the method comprising applying glufosinate herbicide to the cotton crop.

16. A part of the cotton plant of claim 8, wherein the part is selected from the group consisting of pollen, ovule, flowers, bolls, shoots, roots, and leaves, wherein the part comprises the polynucleotide of SEQ ID NO:17.

17. A cotton meal or cotton oil produced from the cotton plant of claim 8, wherein the cotton meal or cotton oil comprises the polynucleotide of SEQ ID NO:17.

* * * * *

SEQUENCE LISTING

```
<160> NUMBER OF SEQ ID NOS: 17

<210> SEQ ID NO 1
<211> LENGTH: 3205
<212> TYPE: DNA
<213> ORGANISM: Artificial Sequence
```

<220> FEATURE:
<223> OTHER INFORMATION: 5' DNA flanking border sequence for cotton event pDAB4468.18.07.1

<400> SEQUENCE: 1

```
catggttcca acaaatgagt acaaatttgc atttgggtcc tcacatttaa caatagcttt     60

aaagtcccga aagttatagt cattatgtaa ggatgaagtt acctctagtg cttgtttgag    120

tttcaaattt gtttctccat caaggttcat ggtctcaaca taacagactg catcctcgta    180

actggatgca agcaagatga ggtctgttgg aaagaattca tctttctcca cctttacaat    240

atctcccact ctaagattct tccattcagt atgatgaaag ttgccatcac cttgatgaac    300

ttttaccttt ctgttgttca cctctatatc ctgaagaaat tccagattga acaagaaatt    360

ttagaacaaa gaaaacaacc aggttatgga aactttacgt ataagctaat tttgcagttc    420

taagatgcat ctggctcaat ctaacgagca gcaagatagt agtgtaaaga aagttcaatg    480

tctatggcac caacgaagac caatatttaa ggtagacaga gaattgagtt acacatagct    540

tagttaaaac aactcgatat accaaaagga aaaattaaaa gtgaaagata gatgtatttt    600

atggcaatca agaaggccta gagatccaga aaaaggaaga agctattgaa gaatatgttc    660

tgatcctttt taaaggccta aatgcacttg gcacaattat attaggcaaa tggaagcact    720

tacaatcatg taaactattt aagaagccct ttctataaat gactatatat tttatggact    780

ccataaaggg aaagatgata gagaaagtaa aaaataagga gtgcaaaggg aagcaactat    840

ctggcacctt aagtagcaac taaaaagaaa tgaagcagca gcagcagcaa agcgaaaaga    900

aagaaggtaa taaagtaaat aaagaaggga gtgaaacctg ctgttgtcgg cgccaatcct    960

caacaccttc tttgatcata gtagcgccaa taacgatgat gagagggacg atagcactaa   1020

gagcggaata aggagcaata gcagtgaagg aaagaatacc agtgaccaaa aagaagaagt   1080

tggcgaccct cctgaattgc tcgaacaagg acttgggcaa gaatgtagca acggtatact   1140

tggtagtact gacataatta tcagagtaat tacgggttcc cgcctccaag gaatttggtt   1200

cattacaata aacaatcctg gaaaatcccg gccccccaat ctgggagtgg tcttccttga   1260

atgatgcttt accacatgca accccataga tcctgctcat caacaccttt ctcctcctac   1320

caccactcat tttccttgtt tctctcttta gctacaaatt aattaattaa ctttatgcag   1380

ctttaatttc ttcacccccc ccccactaat atgtgcccct ttgatcttaa tttcacccta   1440

acagtgtatg tacggtatgt ttgtacatat gcattcaact ataagaagaa gaagaaaatt   1500

tatataaaat aaagcagagg atcccagttt acaaaaaaaa aaaaaaaaga ccaacgcaga   1560

taaagcctgg gttgttgctg tttaactcaa agtcccagaa aatgaacaaa tacaagaaat   1620

aaataataga atattttccc caggcagaaa gtgaataaag gtttagactt taaggagaga   1680

gagagagaga ggaagaagaa gaagaagaag aaatagatag ctttggacaa aggaaaacac   1740

tacattaaag atacaaatat ataaggatat atatatatgt atgtaagcat gtaagattta   1800

gtcttgaaaa gagaaagtgt tgagaaacag ggtgaaggga gaatatataa atttaaaacg   1860

gttttgttta atcaagatat taggaagatg gcgctgttat tgaggtcatc aactgaaaac   1920

acacaaaaac gaagaagcga agaaaaatat tggaagttga aagttcagat gatactacat   1980

gaataaattt tcttcagatg atactacatg aataaatttt ctttcctcgt tttatttctg   2040

tatcttcagc tgaagctttg atttgaacgg tgactttgat tttgatgact ttcttttttt   2100

cttttttctt ttttttttt ttatgtgttc tatgtacgcg cattttgatt ttccctttttg   2160

gaggccaaga caaaagaaaa ttaatactag ctccaaatat aaaattcaaa ctttttgtat   2220
```

```
atttgtgca tatggatatt taatttacgt ctaattcttc tttcaatccc tctactcttt   2280

tcatatttaa attttagtct ctctactttt ggtctttgaa atttattcct taatttaata   2340

attacgatcc aattaaataa tattgtcaaa ccacttctaa taaattgaat tatgtagtat   2400

ttttaaaata aaagtttgct cacagtgact aacattacat ggaaaactaa aaatgttaaa   2460

tataatgttg taacgaattt aaaattataa gatttttcaa tactatttga gagaagtaag   2520

atgaaagtcg attttttttc ttatttacat gatttttcttt ctatcaaagt ttttaataat   2580

tggatttcaa taattaaata taatgaattt ttttaataaa acattaaatg ttattactaa   2640

ttgctagagg catcgattat tacaacatcg tgaattacat caataagaaa gaaaaatgaa   2700

taaactagaa aaaaaaatct agtaaaaata tccggacaca aaaaatatta acaaagaaag   2760

agaaatgatg tataaagcag gattttttac ctaagtaata ttaaaaaaaa acttaaatgg   2820

catgttgcaa aaattatgta ctaaaatagt acgttcaaat gggtggaggg tggtgcatag   2880

acaaaccagt cagcatcatc acaccaaaag ttaggcccga atagtttgaa attagaaagc   2940

tcgcaattga ggtctacagg ccaaattcgc tcttagccgt acaatattac tcaccggatc   3000

ctaaccggtg tgatcatggg ccgcgattaa aaatctcaat tatatttggt ctaatttagt   3060

ttggtattga gtaaaacaaa ttcgaaccaa accaaaatat aaatatatag tttttatata   3120

tatgccttta agacttttta tagaattttc tttaaaaaat atctagaaat atttgcgact   3180

cttctggcat gtaatatttc gttaa                                         3205


<210> SEQ ID NO 2
<211> LENGTH: 1049
<212> TYPE: DNA
<213> ORGANISM: Artificial Sequence
<220> FEATURE:
<223> OTHER INFORMATION: 3' DNA flanking border sequence for cotton
      event pDAB4468.18.07.1

<400> SEQUENCE: 2

gcacatagac acacacatca tctcattgat gcttggtaat aattgtcatt agattgtttt     60

tatgcataga tgcactcgaa atcagccaat tttagacaag tatcaaacgg atgtgacttc    120

agtacattaa aaacgtccgc aatgtgtagt gtctatctga taggcggcac tggtggtgcc    180

tatctgatag acgacacacc tagtattccc cccccacact cccccatcca gctcatttta    240

aatatttatt aaaacaccta aattttatat gttgttttta attataaaaa aaataccaaa    300

cagttttgtc cacatcatat tttttgctat actacactaa caaaataaat atatcttata    360

aattccaact taaactccaa cttaatggtc tcattcacaa atttcatctc aatggtttaa    420

tcttttacct acataaaaaa acaaaaaaat tatattaaaa taataaaaat aacatgccaa    480

taaaaaatat aacaaaaata taacataaat gatacataat aaatacgaat attattatta    540

ttttaaaatg ataataagta aaatgttttg gtttaaaata taatatatat aaaacatgcc    600

aacttaatta ttgtcaaaaa atatcatttt tttgcataca acttcaaaag aaatcttatt    660

ttaatattta taaaaaacat aaaataaaat ttaaaaacat aaactcttat tctcaataaa    720

ctcttattct caattataaa atcttaaaaa attagaacat ataaactaat tcctaattta    780

tctaataaat tacaaattcc atatcaatgg tctcatcttt tacctacata aaaaaataaa    840

aataaaaata ttaaaataat taaaataaca tgccaaataa attttataaa aaaataaatc    900

taatcaacct aaaacacaca taacaaataa attacataaa aaataaaata ttttttgtac    960
```

ataacataaa taggtttttt ttacttcaat aaatattaaa aataaattat gaatgaatga 1020
aaatataaaa taaatacaaa catacatta 1049

<210> SEQ ID NO 3
<211> LENGTH: 6368
<212> TYPE: DNA
<213> ORGANISM: Artificial Sequence
<220> FEATURE:
<223> OTHER INFORMATION: T-strand DNA sequence of pDAB4468

<400> SEQUENCE: 3
ccagtcagca tcatcacacc aaaagttagg cccgaatagt ttgaaattag aaagctcgca 60
attgaggtct acaggccaaa ttcgctctta gccgtacaat attactcacc ggatcctaac 120
cggtgtgatc atgggccgcg attaaaaatc tcaattatat ttggtctaat ttagtttggt 180
attgagtaaa acaaattcga accaaaccaa aatataaata tatagttttt atatatatgc 240
ctttaagact ttttatagaa ttttctttaa aaaatatcta gaaatatttg cgactcttct 300
ggcatgtaat atttcgttaa atatgaagtg ctccattttt attaacttta aataattggt 360
tgtacgatca ctttcttatc aagtgttact aaaatgcgtc aatctctttg ttcttccata 420
ttcatatgtc aaaacctatc aaaattctta tatatctttt tcgaatttga agtgaaattt 480
cgataattta aaattaaata gaacatatca ttatttaggt atcatattga tttttatact 540
taattactaa atttggttaa ctttgaaagt gtacatcaac gaaaaattag tcaaacgact 600
aaaataaata aatatcatgt gttattaaga aaattctcct ataagaatat tttaatagat 660
catatgtttg taaaaaaaat taatttttac taacacatat atttacttat caaaaatttg 720
acaaagtaag attaaaataa tattcatcta acaaaaaaaa aaccagaaaa tgctgaaaac 780
ccggcaaaac cgaaccaatc caaaccgata tagttggttt ggtttgattt tgatataaac 840
cgaaccaact cggtccattt gcacccctaa tcataatagc tttaatattt caagatatta 900
ttaagttaac gttgtcaata tcctggaaat tttgcaaaat gaatcaagcc tatatggctg 960
taatatgaat ttaaaagcag ctcgatgtgg tggtaatatg taatttactt gattctaaaa 1020
aaatatccca agtattaata atttctgcta ggaagaaggt tagctacgat ttacagcaaa 1080
gccagaatac aatgaaccat aaagtgattg aagctcgaaa tatacgaagg aacaaatatt 1140
tttaaaaaaa tacgcaatga cttggaacaa aagaaagtga tatatttttt gttcttaaac 1200
aagcatcccc tctaaagaat ggcagttttc ctttgcatgt aactattatg ctcccttcgt 1260
tacaaaaatt ttggactact attgggaact tcttctgaaa atagtggcca ccgcttaatt 1320
aaggcgcgcc atgcccgggc aagcggccgc acaagtttgt acaaaaaagc aggctccgcg 1380
gtgactgact gaaaagcttg tcgacctgca ggtcaacgga tcaggatatt cttgtttaag 1440
atgttgaact ctatggaggt ttgtatgaac tgatgatcta ggaccggata agttcccttc 1500
ttcatagcga acttattcaa agaatgtttt gtgtatcatt cttgttacat tgttattaat 1560
gaaaaaatat tattggtcat tggactgaac acgagtgtta aatatggacc aggccccaaa 1620
taagatccat tgatatatga attaaataac aagaataaat cgagtcacca aaccacttgc 1680 ctttttttaac gagacttgtt caccaacttg atacaaaagt cattatccta tgcaaatcaa 1740
taatcataca aaaatatcca ataacactaa aaaattaaaa gaaatggata atttcacaat 1800
atgttatacg ataaagaagt tacttttcca agaaattcac tgattttata agcccacttg 1860
cattagataa atggcaaaaa aaaacaaaaa ggaaaagaaa taaagcacga agaattctag 1920
aaaatacgaa atacgcttca atgcagtggg acccacggtt caattattgc caattttcag 1980

```
ctccaccgta tatttaaaaa ataaaacgat aatgctaaaa aaatataaat cgtaacgatc   2040

gttaaatctc aacggctgga tcttatgacg accgttagaa attgtggttg tcgacgagtc   2100

agtaataaac ggcgtcaaag tggttgcagc cggcacacac gagtcgtgtt tatcaactca   2160

aagcacaaat acttttcctc aacctaaaaa taaggcaatt agccaaaaac aactttgcgt   2220

gtaaacaacg ctcaatacac gtgtcatttt attattagct attgcttcac cgccttagct   2280

ttctcgtgac ctagtcgtcc tcgtcttttc ttcttcttct tctataaaac aatacccaaa   2340

gcttcttctt cacaattcag atttcaattt ctcaaaatct taaaaacttt ctctcaattc   2400

tctctaccgt gatcaaggta aatttctgtg ttccttattc tctcaaaatc ttcgattttg   2460

ttttcgttcg atcccaattt cgtatatgtt ctttggttta gattctgtta atcttagatc   2520

gaagacgatt ttctgggttt gatcgttaga tatcatctta attctcgatt agggtttcat   2580

aaatatcatc cgatttgttc aaataatttg agttttgtcg aataattact cttcgatttg   2640

tgatttctat ctagatctgg tgttagtttc tagtttgtgc gatcgaattt gtcgattaat   2700

ctgagttttt ctgattaaca gagatctcca tggctcagac cactctccaa atcacaccca   2760

ctggtgccac cttgggtgcc acagtcactg gtgttcacct tgccacactt gacgatgctg   2820

gtttcgctgc cctccatgca gcctggcttc aacatgcact cttgatcttc cctgggcaac   2880

acctcagcaa tgaccaacag attacctttg ctaaacgctt tggagcaatt gagaggattg   2940

gcggaggtga cattgttgcc atatccaatg tcaaggcaga tggcacagtg cgccagcact   3000

ctcctgctga gtgggatgac atgatgaagg tcattgtggg caacatggcc tggcacgccg   3060

actcaaccta catgccagtc atggctcaag gagctgtgtt cagcgcagaa gttgtcccag   3120

cagttggggg cagaacctgc tttgctgaca tgagggcagc ctacgatgcc cttgatgagg   3180

caacccgtgc tcttgttcac caaaggtctg ctcgtcactc ccttgtgtat tctcagagca   3240

agttgggaca tgtccaacag gccgggtcag cctacatagg ttatggcatg gacaccactg   3300

caactcctct cagaccattg gtcaaggtgc atcctgagac tggaaggccc agcctcttga   3360

tcggccgcca tgcccatgcc atccctggca tggatgcagc tgaatcagag cgcttccttg   3420

aaggacttgt tgactgggcc tgccaggctc ccagagtcca tgctcaccaa tgggctgctg   3480

gagatgtggt tgtgtgggac aaccgctgtt tgctccaccg tgctgagccc tgggatttca   3540

agttgccacg tgtgatgtgg cactccagac tcgctggacg cccagaaact gagggtgctg   3600

ccttggtttg agtagttagc ttaatcacct agagctcggt caccagcata atttttatta   3660

atgtactaaa ttactgtttt gttaaatgca attttgcttt ctcgggattt taatatcaaa   3720

atctatttag aaatacacaa tattttgttg caggcttgct ggagaatcga tctgctatca   3780

taaaaattac aaaaaaattt tatttgcctc aattatttta ggattggtat taaggacgct   3840

taaattattt gtcgggtcac tacgcatcat tgtgattgag aagatcagcg atacgaaata   3900

ttcgtagtac tatcgataat ttatttgaaa attcataaga aaagcaaacg ttacatgaat   3960

tgatgaaaca atacaaagac agataaagcc acgcacattt aggatattgg ccgagattac   4020

tgaatattga gtaagatcac ggaatttctg acaggagcat gtcttcaatt cagcccaaat   4080

ggcagttgaa atactcaaac cgccccatat gcaggagcgg atcattcatt gtttgtttgg   4140

ttgcctttgc caacatggga gtccaaggtt gcggccgcgc gccgacccag ctttcttgta   4200

caaagtggtt gcggccgctt aattaaattt aaatgcccgg gcgtttaaac gcggccgctt   4260

aattaaggcc ggcctgcagc aaacccagaa ggtaattatc caagatgtag catcaagaat   4320

ccaatgttta cgggaaaaac tatggaagta ttatgtaagc tcagcaagaa gcagatcaat   4380
```

```
atgcggcaca tatgcaacct atgttcaaaa atgaagaatg tacagataca agatcctata   4440
ctgccagaat acgaagaaga atacgtagaa attgaaaaag aagaaccagg cgaagaaaag   4500
aatcttgaag acgtaagcac tgacgacaac aatgaaaaga agaagataag gtcggtgatt   4560
gtgaaagaga catagaggac acatgtaagg tggaaaatgt aagggcggaa agtaacctta   4620
tcacaaagga atcttatccc ccactactta tccttttata tttttccgtg tcatttttgc   4680
ccttgagttt tcctatataa ggaaccaagt tcggcatttg tgaaaacaag aaaaaatttg   4740
gtgtaagcta ttttctttga agtactgagg atacaacttc agagaaattt gtaagtttgt   4800
agatctccat gtctccggag aggagaccag ttgagattag gccagctaca gcagctgata   4860
tggccgcggt ttgtgatatc gttaaccatt acattgagac gtctacagtg aactttagga   4920
cagagccaca aacaccacaa gagtggattg atgatctaga gaggttgcaa gatagatacc   4980
cttggttggt tgctgaggtt gagggtgttg tggctggtat tgcttacgct gggccctgga   5040
aggctaggaa cgcttacgat tggacagttg agagtactgt ttacgtgtca cataggcatc   5100
aaaggttggg cctaggatcc acattgtaca cacatttgct taagtctatg gaggcgcaag   5160
gttttaagtc tgtggttgct gttataggcc ttccaaacga tccatctgtt aggttgcatg   5220
aggctttggg atacacagcc cggggtacat tgcgcgcagc tggatacaag catggtggat   5280
ggcatgatgt tggtttttgg caaagggatt ttgagttgcc agctcctcca aggccagtta   5340
ggccagttac ccagatctga ggtaccctga gcttgagctt atgagcttat gagcttagag   5400
ctcggatcca ctagtaacgg ccgccagtgt gctggaattc gcccttgact agataggcgc   5460
ccagatcggc ggcaatagct tcttagcgcc atcccgggtt gatcctatct gtgttgaaat   5520
agttgcggtg ggcaaggctc tctttcagaa agacaggcgg ccaaaggaac ccaaggtgag   5580
gtgggctatg gctctcagtt ccttgtggaa gcgcttggtc taaggtgcag aggtgttagc   5640
gggatgaagc aaaagtgtcc gattgtaaca agatatgttg atcctacgta aggatattaa   5700
agtatgtatt catcactaat ataatcagtg tattccaata tgtactacga tttccaatgt   5760
ctttattgtc gccgtatgta atcggcgtca caaaataatc cccggtgact ttcttttaat   5820
ccaggatgaa ataatatgtt attataattt ttgcgatttg gtccgttata ggaattgaag   5880
tgtgcttgcg gtcgccacca ctcccatttc ataattttac atgtatttga aaaataaaaa   5940
tttatggtat tcaatttaaa cacgtatact tgtaaagaat gatatcttga aagaaatata   6000
gtttaaatat ttattgataa aataacaagt caggtattat agtccaagca aaaacataaa   6060
tttattgatg caagtttaaa ttcagaaata tttcaataac tgattatatc agctggtaca   6120
ttgccgtaga tgaaagactg agtgcgatat tatggtgtaa tacatagcgg ccgggtttct   6180
agtcaccggt taggatccgt ttaaactcga ggctagcgca tgcacataga cacacacatc   6240
atctcattga tgcttggtaa taattgtcat tagattgttt ttatgcatag atgcactcga   6300
aatcagccaa ttttagacaa gtatcaaacg gatgtgactt cagtacatta aaaacgtccg   6360
caatgtgt                                                            6368
```

<210> SEQ ID NO 4
<211> LENGTH: 29
<212> TYPE: DNA
<213> ORGANISM: Artificial Sequence
<220> FEATURE:
<223> OTHER INFORMATION: 1807_3end_genome1 primer sequence

<400> SEQUENCE: 4

```
tgtaggtaaa agattaaacc attgagatg                                      29
```

<210> SEQ ID NO 5
<211> LENGTH: 28
<212> TYPE: DNA
<213> ORGANISM: Artificial Sequence
<220> FEATURE:
<223> OTHER INFORMATION: 1807_3end_genome2 primer sequence

<400> SEQUENCE: 5
tgtgtgtttt aggttgatta gatttatt 28

<210> SEQ ID NO 6
<211> LENGTH: 30
<212> TYPE: DNA
<213> ORGANISM: Artificial Sequence
<220> FEATURE:
<223> OTHER INFORMATION: 1807_3end_genome3 primer sequence

<400> SEQUENCE: 6
tgagaataag agttatttga gaataagagt 30

<210> SEQ ID NO 7
<211> LENGTH: 29
<212> TYPE: DNA
<213> ORGANISM: Artificial Sequence
<220> FEATURE:
<223> OTHER INFORMATION: 1807_5end_genome1 primer sequence

<400> SEQUENCE: 7
gaaagagaaa tgatgtataa agcaggatt 29

<210> SEQ ID NO 8
<211> LENGTH: 28
<212> TYPE: DNA
<213> ORGANISM: Artificial Sequence
<220> FEATURE:
<223> OTHER INFORMATION: 1807_5end_genome2 primer sequence

<400> SEQUENCE: 8
tgctcacagt gactaacatt acatggaa 28

<210> SEQ ID NO 9
<211> LENGTH: 28
<212> TYPE: DNA
<213> ORGANISM: Artificial Sequence
<220> FEATURE:
<223> OTHER INFORMATION: 1807_5end_genome3 primer sequence

<400> SEQUENCE: 9
ctatttgaga gaagtaagat gaaagtcg 28

<210> SEQ ID NO 10
<211> LENGTH: 30
<212> TYPE: DNA
<213> ORGANISM: Artificial Sequence
<220> FEATURE:
<223> OTHER INFORMATION: 1807_5end_genome4 primer sequence

<400> SEQUENCE: 10
acaacatcgt gaattacatc aataagaaag 30

<210> SEQ ID NO 11
<211> LENGTH: 17
<212> TYPE: DNA
<213> ORGANISM: Artificial Sequence
<220> FEATURE:
<223> OTHER INFORMATION: aad12_N1_primer primer sequence

<400> SEQUENCE: 11
gtgttgccca gggaaga 17

<210> SEQ ID NO 12
<211> LENGTH: 18
<212> TYPE: DNA
<213> ORGANISM: Artificial Sequence
<220> FEATURE:
<223> OTHER INFORMATION: aad12_N2_primer primer sequence

<400> SEQUENCE: 12
atgttgaagc caggctgc 18

<210> SEQ ID NO 13
<211> LENGTH: 24
<212> TYPE: DNA
<213> ORGANISM: Artificial Sequence
<220> FEATURE:
<223> OTHER INFORMATION: ubi.for.primer primer sequence

<400> SEQUENCE: 13
cacagaaatt taccttgatc acgg 24

<210> SEQ ID NO 14
<211> LENGTH: 24
<212> TYPE: DNA
<213> ORGANISM: Artificial Sequence
<220> FEATURE:
<223> OTHER INFORMATION: PAT.EXPRESSION CASSETTE.F_primer primer sequence

<400> SEQUENCE: 14
ccagaaggta attatccaag atgt 24

<210> SEQ ID NO 15
<211> LENGTH: 24
<212> TYPE: DNA
<213> ORGANISM: Artificial Sequence
<220> FEATURE:
<223> OTHER INFORMATION: PAT.GOI.Primer primer sequence

<400> SEQUENCE: 15
gacagagcca caaacaccac aaga 24

<210> SEQ ID NO 16
<211> LENGTH: 21
<212> TYPE: DNA
<213> ORGANISM: Artificial Sequence
<220> FEATURE:
<223> OTHER INFORMATION: Orf.F.Primer primer sequence

<400> SEQUENCE: 16
agatcggcgg caatagcttc t 21

<210> SEQ ID NO 17
<211> LENGTH: 10155
<212> TYPE: DNA
<213> ORGANISM: Artificial Sequence
<220> FEATURE:
<223> OTHER INFORMATION: The expected sequence of cotton event pDAB4468.18.07.1, including the 5' genomic flanking sequence, pDAB4468 T-strand insert, and 3' genomic flanking sequence.

<400> SEQUENCE: 17

```
catggttcca acaaatgagt acaaatttgc atttgggtcc tcacatttaa caatagcttt     60
aaagtcccga aagttatagt cattatgtaa ggatgaagtt acctctagtg cttgtttgag    120
tttcaaattt gtttctccat caaggttcat ggtctcaaca taacagactg catcctcgta    180
actggatgca agcaagatga ggtctgttgg aaagaattca tctttctcca cctttacaat    240
atctcccact ctaagattct tccattcagt atgatgaaag ttgccatcac cttgatgaac    300
ttttaccttt ctgttgttca cctctatatc ctgaagaaat tccagattga acaagaaatt    360
ttagaacaaa gaaaacaacc aggttatgga aactttacgt ataagctaat tttgcagttc    420
taagatgcat ctggctcaat ctaacgagca gcaagatagt agtgtaaaga aagttcaatg    480
tctatggcac caacgaagac caatatttaa ggtagacaga gaattgagtt acacatagct    540
tagttaaaac aactcgatat accaaaagga aaaattaaaa gtgaaagata gatgtatttt    600
atggcaatca agaaggccta gagatccaga aaaaggaaga agctattgaa gaatatgttc    660
tgatcctttt taaaggccta aatgcacttg gcacaattat attaggcaaa tggaagcact    720
tacaatcatg taaactattt aagaagccct ttctataaat gactatatat tttatggact    780
ccataaaggg aaagatgata gagaaagtaa aaaataagga gtgcaaaggg aagcaactat    840
ctggcacctt aagtagcaac taaaaagaaa tgaagcagca gcagcagcaa agcgaaaaga    900
aagaaggtaa taaagtaaat aaagaaggga gtgaaacctg ctgttgtcgg cgccaatcct    960
caacaccttc tttgatcata gtagcgccaa taacgatgat gagagggacg atagcactaa   1020
gagcggaata aggagcaata gcagtgaagg aaagaatacc agtgaccaaa aagaagaagt   1080
tggcgaccct cctgaattgc tcgaacaagg acttgggcaa gaatgtagca acggtatact   1140
tggtagtact gacataatta tcagagtaat tacgggttcc cgcctccaag gaatttggtt   1200
cattacaata aacaatcctg gaaaatcccg gccccccaat ctgggagtgg tcttccttga   1260
atgatgcttt accacatgca accccataga tcctgctcat caacaccttt ctcctcctac   1320
caccactcat tttccttgtt tctctcttta gctacaaatt aattaattaa ctttatgcag   1380
ctttaatttc ttcacccccc ccccactaat atgtgcccct ttgatcttaa tttcacccta   1440
acagtgtatg tacggtatgt ttgtacatat gcattcaact ataagaagaa gaagaaaatt   1500
tatataaaat aaagcagagg atcccagttt acaaaaaaaa aaaaaaaaga ccaacgcaga   1560
taaagcctgg gttgttgctg tttaactcaa agtcccagaa aatgaacaaa tacaagaaat   1620
aaataataga atattttccc caggcagaaa gtgaataaag gtttagactt taaggagaga   1680
gagagagaga ggaagaagaa gaagaagaag aaatagatag ctttggacaa aggaaaacac   1740
tacattaaag atacaaatat ataaggatat atatatatgt atgtaagcat gtaagattta   1800
gtcttgaaaa gagaaagtgt tgagaaacag ggtgaaggga gaatatataa atttaaaacg   1860
gttttgttta atcaagatat taggaagatg gcgctgttat tgaggtcatc aactgaaaac   1920
acacaaaaac gaagaagcga agaaaaatat tggaagttga aagttcagat gatactacat   1980
gaataaattt tcttcagatg atactacatg aataaatttt ctttcctcgt tttatttctg   2040
tatcttcagc tgaagctttg atttgaacgg tgactttgat tttgatgact ttcttttttt   2100
cttttttttct ttttttttt ttatgtgttc tatgtacgcg cattttgatt ttccctttg    2160
gaggccaaga caaaagaaaa ttaatactag ctccaaatat aaaattcaaa ctttttgtat   2220
attttgtgca tatggatatt taatttacgt ctaattcttc tttcaatccc tctactcttt   2280
tcatatttaa attttagtct ctctactttt ggtctttgaa atttattcct taatttaata   2340
```

```
attacgatcc aattaaataa tattgtcaaa ccacttctaa taaattgaat tatgtagtat   2400
ttttaaaata aaagtttgct cacagtgact aacattacat ggaaaactaa aaatgttaaa   2460
tataatgttg taacgaattt aaaattataa gatttttcaa tactatttga gagaagtaag   2520
atgaaagtcg atttttttc ttatttacat gattttcttt ctatcaaagt ttttaataat   2580
tggatttcaa taattaaata taatgaattt ttttaataaa acattaaatg ttattactaa   2640
ttgctagagg catcgattat tacaacatcg tgaattacat caataagaaa gaaaaatgaa   2700
taaactagaa aaaaaaatct agtaaaaata tccggacaca aaaaatatta acaaagaaag   2760
agaaatgatg tataaagcag gattttttac ctaagtaata ttaaaaaaaa acttaaatgg   2820
catgttgcaa aaattatgta ctaaaatagt acgttcaaat gggtggaggg tggtgcatag   2880
acaaaccagt cagcatcatc acaccaaaag ttaggcccga atagtttgaa attagaaagc   2940
tcgcaattga ggtctacagg ccaaattcgc tcttagccgt acaatattac tcaccggatc   3000
ctaaccggtg tgatcatggg ccgcgattaa aaatctcaat tatatttggt ctaatttagt   3060
ttggtattga gtaaaacaaa ttcgaaccaa accaaaatat aaatatatag tttttatata   3120
tatgccttta agacttttta tagaattttc tttaaaaaat atctagaaat atttgcgact   3180
cttctggcat gtaatatttc gttaaatatg aagtgctcca tttttattaa ctttaaataa   3240
ttggttgtac gatcactttc ttatcaagtg ttactaaaat gcgtcaatct ctttgttctt   3300
ccatattcat atgtcaaaac ctatcaaaat tcttatatat ctttttcgaa tttgaagtga   3360
aatttcgata atttaaaatt aaatagaaca tatcattatt taggtatcat attgattttt   3420
atacttaatt actaaatttg gttaactttg aaagtgtaca tcaacgaaaa attagtcaaa   3480
cgactaaaat aaataaatat catgtgttat taagaaaatt ctcctataag aatattttaa   3540
tagatcatat gtttgtaaaa aaaattaatt tttactaaca catatattta cttatcaaaa   3600
atttgacaaa gtaagattaa aataatattc atctaacaaa aaaaaaacca gaaaatgctg   3660
aaaacccggc aaaaccgaac caatccaaac cgatatagtt ggtttggttt gattttgata   3720
taaaccgaac caactcggtc catttgcacc cctaatcata atagctttaa tatttcaaga   3780
tattattaag ttaacgttgt caatatcctg gaaattttgc aaaatgaatc aagcctatat   3840
ggctgtaata tgaatttaaa agcagctcga tgtggtggta atatgtaatt tacttgattc   3900
taaaaaaata tcccaagtat taataatttc tgctaggaag aaggttagct acgatttaca   3960
gcaaagccag aatacaatga accataaagt gattgaagct cgaaatatac gaaggaacaa   4020
atatttttaa aaaaatacgc aatgacttgg aacaaaagaa agtgatatat tttttgttct   4080
taaacaagca tcccctctaa agaatggcag ttttcctttg catgtaacta ttatgctccc   4140
ttcgttacaa aaattttgga ctactattgg gaacttcttc tgaaaatagt ggccaccgct   4200
taattaaggc gcgccatgcc cgggcaagcg gccgcacaag tttgtacaaa aaagcaggct   4260
ccgcggtgac tgactgaaaa gcttgtcgac ctgcaggtca acggatcagg atattcttgt   4320
ttaagatgtt gaactctatg gaggtttgta tgaactgatg atctaggacc ggataagttc   4380
ccttcttcat agcgaactta ttcaaagaat gttttgtgta tcattcttgt tacattgtta   4440
ttaatgaaaa aatattattg gtcattggac tgaacacgag tgttaaatat ggaccaggcc   4500
ccaaataaga tccattgata tatgaattaa ataacaagaa taaatcgagt caccaaacca   4560
cttgcctttt ttaacgagac ttgttcacca acttgataca aaagtcatta tcctatgcaa   4620
atcaataatc atacaaaaat atccaataac actaaaaaat taaaagaaat ggataatttc   4680
acaatatgtt atacgataaa gaagttactt ttccaagaaa ttcactgatt ttataagccc   4740
```

-continued

```
acttgcatta gataaatggc aaaaaaaaac aaaaaggaaa agaaataaag cacgaagaat   4800
tctagaaaat acgaaatacg cttcaatgca gtgggaccca cggttcaatt attgccaatt   4860
ttcagctcca ccgtatattt aaaaaataaa acgataatgc taaaaaaata taaatcgtaa   4920
cgatcgttaa atctcaacgg ctggatctta tgacgaccgt tagaaattgt ggttgtcgac   4980
gagtcagtaa taaacggcgt caaagtggtt gcagccggca cacacgagtc gtgtttatca   5040
actcaaagca caaatacttt tcctcaacct aaaaataagg caattagcca aaaacaactt   5100
tgcgtgtaaa caacgctcaa tacacgtgtc attttattat tagctattgc ttcaccgcct   5160
tagctttctc gtgacctagt cgtcctcgtc ttttcttctt cttcttctat aaaacaatac   5220
ccaaagcttc ttcttcacaa ttcagatttc aatttctcaa aatcttaaaa actttctctc   5280
aattctctct accgtgatca aggtaaattt ctgtgttcct tattctctca aaatcttcga   5340
ttttgttttc gttcgatccc aatttcgtat atgttctttg gtttagattc tgttaatctt   5400
agatcgaaga cgattttctg ggtttgatcg ttagatatca tcttaattct cgattagggt   5460
ttcataaata tcatccgatt tgttcaaata atttgagttt tgtcgaataa ttactcttcg   5520
atttgtgatt tctatctaga tctggtgtta gtttctagtt tgtgcgatcg aatttgtcga   5580
ttaatctgag tttttctgat taacagagat ctccatggct cagaccactc tccaaatcac   5640
acccactggt gccaccttgg gtgccacagt cactggtgtt caccttgcca cacttgacga   5700
tgctggtttc gctgccctcc atgcagcctg gcttcaacat gcactcttga tcttccctgg   5760
gcaacacctc agcaatgacc aacagattac ctttgctaaa cgctttggag caattgagag   5820
gattggcgga ggtgacattg ttgccatatc caatgtcaag gcagatggca cagtgcgcca   5880
gcactctcct gctgagtggg atgacatgat gaaggtcatt gtgggcaaca tggcctggca   5940
cgccgactca acctacatgc cagtcatggc tcaaggagct gtgttcagcg cagaagttgt   6000
cccagcagtt gggggcagaa cctgctttgc tgacatgagg gcagcctacg atgcccttga   6060
tgaggcaacc cgtgctcttg ttcaccaaag gtctgctcgt cactcccttg tgtattctca   6120
gagcaagttg ggacatgtcc aacaggccgg gtcagcctac ataggttatg gcatggacac   6180
cactgcaact cctctcagac cattggtcaa ggtgcatcct gagactggaa ggcccagcct   6240
cttgatcggc cgccatgccc atgccatccc tggcatggat gcagctgaat cagagcgctt   6300
ccttgaagga cttgttgact gggcctgcca ggctcccaga gtccatgctc accaatgggc   6360
tgctggagat gtggttgtgt gggacaaccg ctgtttgctc caccgtgctg agccctggga   6420
tttcaagttg ccacgtgtga tgtggcactc cagactcgct ggacgcccag aaactgaggg   6480
tgctgccttg gtttgagtag ttagcttaat cacctagagc tcggtcacca gcataatttt   6540
tattaatgta ctaaattact gttttgttaa atgcaatttt gctttctcgg gattttaata   6600
tcaaaatcta tttagaaata cacaatattt tgttgcaggc ttgctggaga atcgatctgc   6660
tatcataaaa attacaaaaa aattttattt gcctcaatta ttttaggatt ggtattaagg   6720
acgcttaaat tatttgtcgg gtcactacgc atcattgtga ttgagaagat cagcgatacg   6780
aaatattcgt agtactatcg ataatttatt tgaaaattca taagaaaagc aaacgttaca   6840
tgaattgatg aaacaataca aagacagata aagccacgca catttaggat attggccgag   6900
attactgaat attgagtaag atcacggaat ttctgacagg agcatgtctt caattcagcc   6960
caaatggcag ttgaaatact caaaccgccc catatgcagg agcggatcat tcattgtttg   7020
tttggttgcc tttgccaaca tgggagtcca aggttgcggc cgcgcgccga cccagctttc   7080
ttgtacaaag tggttgcggc cgcttaatta aatttaaatg cccgggcgtt taaacgcggc   7140
```

```
cgcttaatta aggccggcct gcagcaaacc cagaaggtaa ttatccaaga tgtagcatca   7200
agaatccaat gtttacggga aaaactatgg aagtattatg taagctcagc aagaagcaga   7260
tcaatatgcg gcacatatgc aacctatgtt caaaaatgaa gaatgtacag atacaagatc   7320
ctatactgcc agaatacgaa gaagaatacg tagaaattga aaaagaagaa ccaggcgaag   7380
aaaagaatct tgaagacgta agcactgacg acaacaatga aaagaagaag ataaggtcgg   7440
tgattgtgaa agagacatag aggacacatg taaggtggaa aatgtaaggg cggaaagtaa   7500
ccttatcaca aaggaatctt atcccccact acttatcctt ttatattttt ccgtgtcatt   7560
tttgcccttg agttttccta tataaggaac caagttcggc atttgtgaaa acaagaaaaa   7620
atttggtgta agctattttc tttgaagtac tgaggataca acttcagaga aatttgtaag   7680
tttgtagatc tccatgtctc cggagaggag accagttgag attaggccag ctacagcagc   7740
tgatatggcc gcggtttgtg atatcgttaa ccattacatt gagacgtcta cagtgaactt   7800
taggacagag ccacaaacac cacaagagtg gattgatgat ctagagaggt tgcaagatag   7860
ataccctttgg ttggttgctg aggttgaggg tgttgtggct ggtattgctt acgctgggcc   7920
ctggaaggct aggaacgctt acgattggac agttgagagt actgtttacg tgtcacatag   7980
gcatcaaagg ttgggcctag gatccacatt gtacacacat ttgcttaagt ctatggaggc   8040
gcaaggtttt aagtctgtgg ttgctgttat aggccttcca aacgatccat ctgttaggtt   8100
gcatgaggct tgggatacat cagcccgggg tacattgcgc gcagctggat acaagcatgg   8160
tggatggcat gatgttggtt tttggcaaag ggattttgag ttgccagctc ctccaaggcc   8220
agttaggcca gttacccaga tctgaggtac cctgagcttg agcttatgag cttatgagct   8280
tagagctcgg atccactagt aacggccgcc agtgtgctgg aattcgccct tgactagata   8340
ggcgcccaga tcggcggcaa tagcttctta gcgccatccc gggttgatcc tatctgtgtt   8400
gaaatagttg cggtgggcaa ggctctcttt cagaaagaca ggcggccaaa ggaacccaag   8460
gtgaggtggg ctatggctct cagttccttg tggaagcgct tggtctaagg tgcagaggtg   8520
ttagcgggat gaagcaaaag tgtccgattg taacaagata tgttgatcct acgtaaggat   8580
attaaagtat gtattcatca ctaatataat cagtgtattc caatatgtac tacgatttcc   8640
aatgtcttta ttgtcgccgt atgtaatcgg cgtcacaaaa taatccccgg tgactttctt   8700
ttaatccagg atgaaataat atgttattat aatttttgcg atttggtccg ttataggaat   8760
tgaagtgtgc ttgcggtcgc caccactccc atttcataat tttacatgta tttgaaaaat   8820
aaaaatttat ggtattcaat ttaaacacgt atacttgtaa agaatgatat cttgaaagaa   8880
atatagttta aatatttatt gataaaataa caagtcaggt attatagtcc aagcaaaaac   8940
ataaatttat tgatgcaagt ttaaattcag aaatatttca ataactgatt atatcagctg   9000
gtacattgcc gtagatgaaa gactgagtgc gatattatgg tgtaatacat agcggccggg   9060
tttctagtca ccggttagga tccgtttaaa ctcgaggcta gcgcatgcac atagacacac   9120
acatcatctc attgatgctt ggtaataatt gtcattagat tgtttttatg catagatgca   9180
ctcgaaatca gccaatttta gacaagtatc aaacggatgt gacttcagta cattaaaaac   9240
gtccgcaatg tgtagtgtct atctgatagg cggcactggt ggtgcctatc tgatagacga   9300
cacacctagt attccccccc cacactcccc catccagctc attttaaata tttattaaaa   9360
cacctaaatt ttatatgttg tttttaatta taaaaaaaat accaaacagt tttgtccaca   9420
tcatattttt tgctatacta cactaacaaa ataaatatat cttataaatt ccaacttaaa   9480
ctccaactta atggtctcat tcacaaattt catctcaatg gtttaatctt ttacctacat   9540
```

-continued

```
aaaaaaacaa aaaaattata ttaaaataat aaaaataaca tgccaataaa aaatataaca   9600

aaaatataac ataaatgata cataataaat acgaatatta ttattatttt aaaatgataa   9660

taagtaaaat gttttggttt aaaatataat atatataaaa catgccaact taattattgt   9720

caaaaaatat cattttttttg catacaactt caaaagaaat cttattttaa tatttataaa   9780

aaacataaaa taaaatttaa aaacataaac tcttattctc aataaactct tattctcaat   9840

tataaaatct taaaaaatta gaacatataa actaattcct aatttatcta ataaattaca   9900

aattccatat caatggtctc atcttttacc tacataaaaa aataaaaata aaaatattaa   9960

aataattaaa ataacatgcc aaataaattt tataaaaaaa taaatctaat caacctaaaa  10020

cacacataac aaataaatta cataaaaaat aaaatatttt ttgtacataa cataaatagg  10080

tttttttac ttcaataaat attaaaaata aattatgaat gaatgaaaat ataaaataaa  10140

tacaaacata catta                                                    10155
```